US007694678B2

(12) United States Patent
Turiello

(10) Patent No.: US 7,694,678 B2
(45) **Date of Patent: *Apr. 13, 2010**

(54) BREATHABLE AIR SAFETY SYSTEM AND METHOD HAVING A FILL STATION

(75) Inventor: Anthony J Turiello, Redwood City, CA (US)

(73) Assignee: Rescue Air Systems, Inc., San Carlos, CA (US)

( * ) Notice: Subject to any disclaimer, the term of this patent is extended or adjusted under 35 U.S.C. 154(b) by 489 days.

This patent is subject to a terminal disclaimer.

(21) Appl. No.: 11/505,599

(22) Filed: Aug. 16, 2006

(65) Prior Publication Data

US 2009/0283151 A1 Nov. 19, 2009

(51) Int. Cl.
*A61M 16/00* (2006.01)
*A62B 9/00* (2006.01)

(52) U.S. Cl. ............................ 128/204.21; 128/200.24; 128/204.18; 128/204.26; 128/205.22

(58) Field of Classification Search ............ 128/200.24, 128/201.24, 203.27, 204.18, 204.21, 205.26, 128/897, 898; 52/2.1, 169.6, 302.1, 173.3; 454/169–172
See application file for complete search history.

(56) References Cited

U.S. PATENT DOCUMENTS 281,027 A * 7/1883 Cottier ........................ 454/368
465,298 A * 12/1891 Smith ........................ 165/48.1
472,163 A * 4/1892 Duffy ........................ 454/252
835,075 A * 11/1906 Mahaffy ................ 128/207.12
1,005,196 A * 10/1911 Gold et al. .................. 454/172
1,413,275 A * 4/1922 Howard ...................... 116/214
2,014,840 A * 9/1935 Geiger et al. ............... 454/252
2,299,793 A * 10/1942 Cannaday et al. ....... 128/202.13
2,855,926 A * 10/1958 Koppelman ............ 128/202.13
3,739,707 A * 6/1973 Knapp ........................ 454/228
3,945,800 A * 3/1976 Roos .......................... 431/345
3,973,562 A * 8/1976 Jansson ................. 128/205.12
3,995,626 A * 12/1976 Pearce, Jr. .............. 128/205.24
4,058,253 A * 11/1977 Munk et al. ............... 236/46 R
4,153,083 A * 5/1979 Imler et al. ..................... 141/4
4,165,738 A * 8/1979 Graves et al. .......... 128/202.13

(Continued)

OTHER PUBLICATIONS

"New Firefighter Air System Makes High-Rise Fire-Fighting Safer; APS Stairwell Air-Replenishment System First of Its Kind in Arizona". Business Wire. Apr. 27, 2004.*

*Primary Examiner*—Justine R Yu
*Assistant Examiner*—Annette F Dixon
(74) *Attorney, Agent, or Firm*—Raj Abhyanker LLP

(57) ABSTRACT

A breathable air safety system and method having a fill station are disclosed. In one aspect, a method of safety of a building structure is described. A prescribed pressure of an emergency support system is ensured to be maintained within a threshold range of the prescribed pressure by including a valve of the emergency support system to prevent leakage of breathable air from the emergency support system. A filling process of a breathable air apparatus is safeguarded by enclosing the breathable air apparatus in a secure chamber of a fill site of the emergency support system of the building structure. The prescribed pressure of the emergency support system is designated based on a municipality code that specifies a pressure rating of the breathable air apparatus. The prescribed pressure of the emergency support system is maintained such that a system pressure is compatible with the breathable air apparatus.

25 Claims, 17 Drawing Sheets

U.S. PATENT DOCUMENTS 4,331,139 A * 5/1982 Popa ..................... 128/202.13
4,353,292 A * 10/1982 Almasi et al. ............... 454/168
4,380,187 A * 4/1983 Wicks ........................ 454/342
4,413,622 A * 11/1983 Austin ................... 128/205.25
4,467,796 A * 8/1984 Beagley ................. 128/202.13
4,510,930 A * 4/1985 Garcia ................... 128/202.22
4,542,774 A * 9/1985 Stavlo ........................... 141/1
4,712,594 A * 12/1987 Schneider ................... 141/114
4,862,931 A * 9/1989 Vella ............................. 141/1
5,131,269 A * 7/1992 Blosnick et al. ............... 73/129
5,570,685 A * 11/1996 Turiello ................. 128/202.13
5,800,260 A * 9/1998 Kao ........................... 454/370
5,809,999 A * 9/1998 Lang ..................... 128/200.24
5,979,440 A * 11/1999 Honkonen et al. ..... 128/201.21
6,474,334 B1 * 11/2002 Lemer ................... 128/204.18
6,701,923 B2 * 3/2004 Cazenave et al. ...... 128/204.22
6,948,498 B2 * 9/2005 Cazenave et al. ...... 128/204.22
7,055,780 B2 * 6/2006 Phillips ................... 244/118.5
7,204,249 B1 * 4/2007 Richey et al. .......... 128/204.18
7,255,104 B2 * 8/2007 Phillips ................. 128/204.22
2006/0219842 A1 * 10/2006 Shell et al. ............... 244/118.5

* cited by examiner

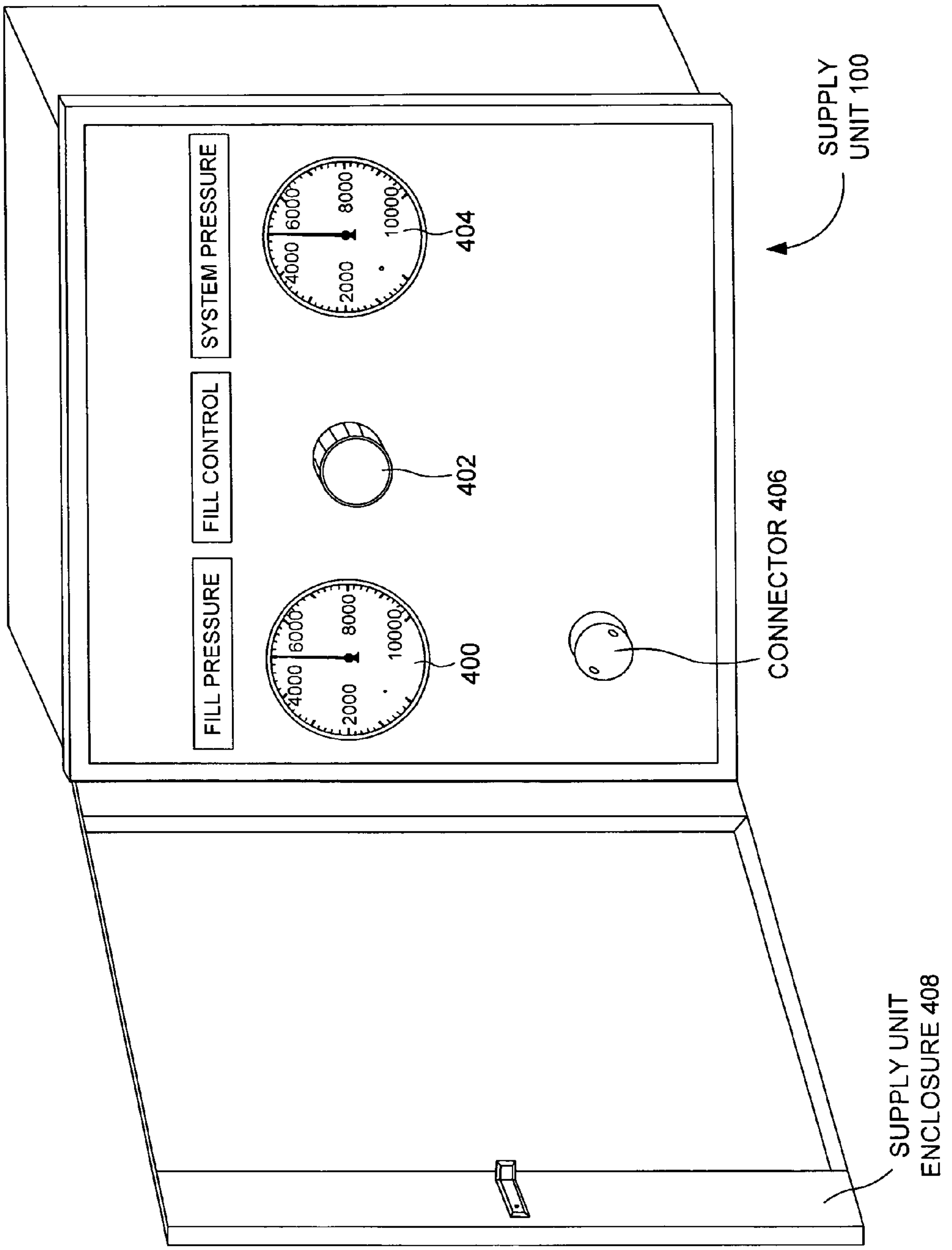
FIGURE 4A (FRONT VIEW)

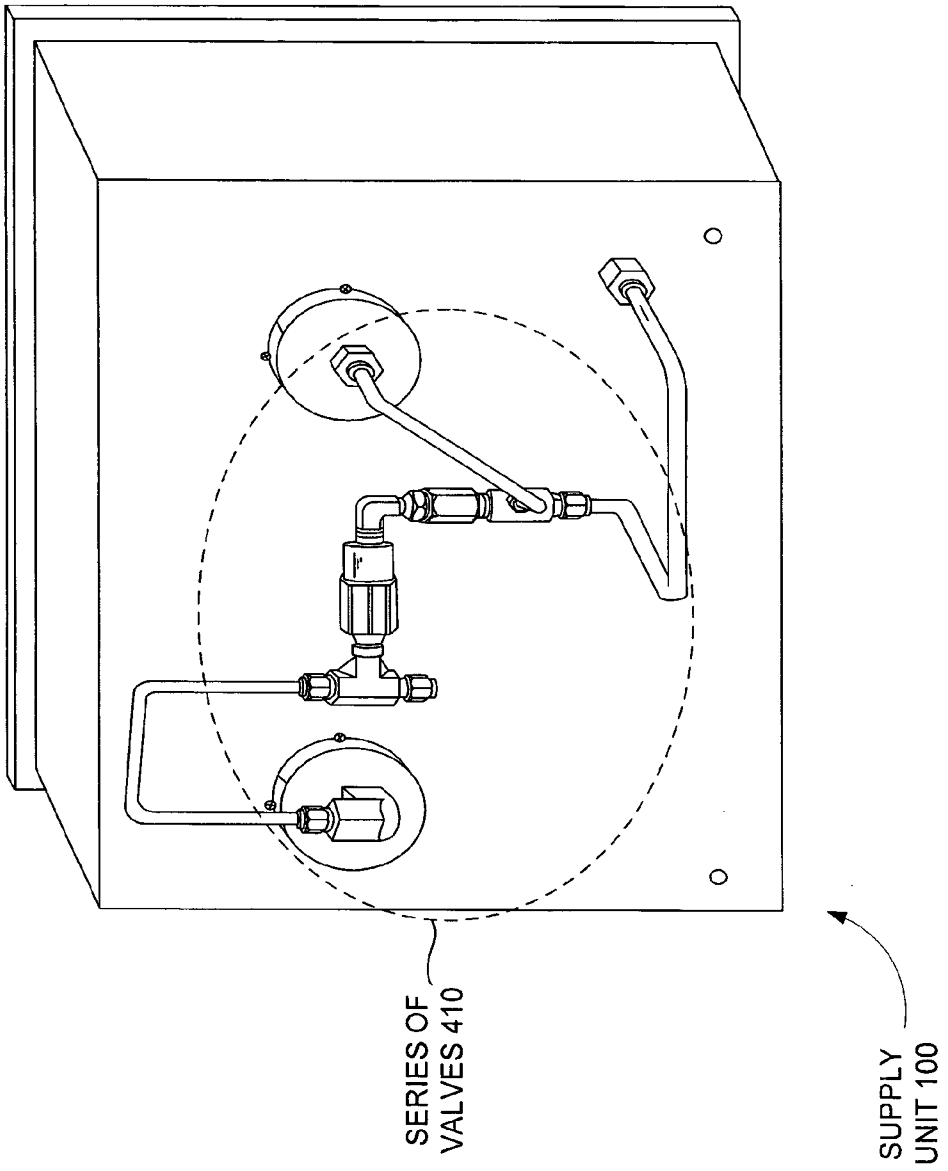
FIGURE 4B (REAR VIEW)

BREATHABLE AIR SAFETY SYSTEM AND METHOD HAVING A FILL STATION

FIELD OF TECHNOLOGY

This disclosure relates generally to the technical fields of safety systems and, in one example embodiment, to a safety system and method having a fill station.

BACKGROUND

In a case of an emergency situation of a structure (e.g., a horizontal building structure such as a shopping mall, IKEA, Home Depot, a vertical building structure such as a high rise building, a mid rise building, and/or a low rise building, a mine, a subway, and/or a tunnel), emergency personnel (e.g., a fire fighter, a SWAT team, a law enforcer, and/or a medical worker, etc.) may be deployed on-site of the building structure to alleviate the emergency situation through mitigating a source of hazard as well as rescuing stranded civilians from the building structure. The emergency situation may include events such as a building fire, a chemical attack, terror attack, subway accident, mine collapse, and/or a biological agent attack.

In such situations, breathable air inside the building structure may be hazardously affected (e.g., depleted, absorbed, and/or contaminated). In addition, flow of fresh air into the building structure may be significantly hindered due to the building structure having enclosed regions, lack of windows, and/or high concentration of contaminants. As a result, inhaling air in the building structure may be extremely detrimental and may further result in death (e.g., within minutes). Furthermore, emergency work may often need to be performed from within the building structure (e.g., due to a limitation of emergency equipment able to be transported on a ground level).

The emergency personnel's ability to alleviate the emergency in an efficient manner may be significantly limited by the lack of breathable air and/or the abundance of contaminated air. A survival rate of stranded civilians in the building structure may substantially decreased due to a propagation of contaminated air throughout the building structure placing a large number of innocent lives at significant risk.

As such, the emergency personnel may utilize a portable breathable air apparatus (e.g., self-contained breathable air apparatus) as a source of breathable air during a rescue mission. However, the portable breathable air apparatus may be heavy (e.g., 20-30 pounds) and may only provide breathable air for a short while (e.g., approximately 15-30 minutes). In the emergency situation, the emergency personnel may need to walk and/or climb to a particular location within the building structure to perform rescuing work due to inoperable transport systems (e.g., obstructed walkway, elevators, moving sidewalks, and/or escalators, etc.). As such, by the time the emergency personnel reaches the particular location, his/her portable breathable air apparatus may have already depleted and may require running back to the ground floor for a new portable breathable air apparatus. As a result, precious lives may be lost due to precious time being lost.

An extra supply of portable breathable air apparatuses may be stored throughout the building structure so that emergency personnel can replace their portable breathable air apparatuses within the building structure. However, supplying structures with spare portable breathable air apparatuses may be expensive and take up space in the building structure severely handicapping the ability of emergency personnel to perform rescue tasks.

Furthermore, the building structure may not regularly inspect the spare portable breathable air apparatuses. With time, the spare portable breathable air apparatuses may experience pressure loss placing the emergency personnel at significant risk when it is utilized in the emergency situation. The spare portable breathable air apparatuses may also be tampered with during storage. Contaminants may be introduced into the spare portable breathable air apparatuses that are detrimental to the emergency personnel.

SUMMARY

A safety system and method having a fill station are disclosed. In one aspect, a safety system of a building structure includes a supply unit of a building structure to facilitate delivery of breathable air from a source of compressed air to an air distribution system of the building structure, a valve to prevent leakage of the breathable air from the air distribution system potentially leading to loss of a system pressure, a fill station interior to the building structure to provide the breathable air to a breathable air apparatus at multiple locations of the building structure, a secure chamber of the fill station as a safety shield that confines a possible rupture of an over-pressurized breathable air apparatus within the secure chamber, and/or a distribution structure that is compatible with use with compressed air that facilitates dissemination of the breathable air of the source of compressed air to multiple locations of the building structure.

The system may include a supply unit enclosure encompassing the supply unit having any of a weather resistant feature, ultraviolet and infrared solar radiation resistant feature to prevent corrosion and physical damage. The system may also include a locking mechanism of the supply unit enclosure to secure the supply unit from intrusions that potentially compromise safety and reliability of the air distribution system. Further, the system may include a robust metallic material of the supply unit enclosure to minimize a physical damage due to various hazards to protect the supply unit from any of an intrusion and damage. The robust metallic material may be at least substantially 18 gauge carbon steel.

The system may also include a valve of the supply unit to perform any of a suspension of transfer and a reduction of flow of breathable air from the source of compressed air to the air distribution system when useful. The system may include a safety relief valve of any of the supply unit and the fill station to release breathable air when a system pressure of the air distribution system exceeds a threshold value beyond the design pressure to ensure reliability of the air distribution system through maintaining the system pressure such that it is within a threshold range of a pressure rating of each component of the air distribution system. Further, any of a CGA connector and a RIC (rapid interventions company/crew)/UAC (universal air connection) connector of the supply unit may be included to facilitate a connection with the source of compressed air through ensuring compatibility with a connector of the source of compressed air. The system may include an adjustable pressure regulator of the supply unit to adjust a fill pressure of the source of compressed air to ensure that the fill pressure does not exceed the design pressure of the air distribution system.

In addition, the system may include at least one pressure gauge of the supply unit enclosure to indicate any of the system pressure of the air distribution system and the fill pressure of the source of compressed air and a visible marking of the supply unit enclosure and the fill station enclosure to provide luminescence in a reduced light environment. The system may include another valve of the fill station to prevent leakage of air from the air distribution system potentially leading to pressure loss of the air distribution system through ensuring that the system pressure is maintained within a threshold range of the design pressure to reliably fill the breathable air apparatus. The system may include an isolation valve of the fill station to isolate a fill station from a remaining portion of the air distribution system. In addition, the isolation valve may be automatically actuated based on an air pressure sensor of the air distribution system.

Further, the system may include at least one pressure regulator of the fill station to adjust the fill pressure to fill the breathable air apparatus and to ensure that the fill pressure does not exceed the pressure rating of the breathable air apparatus resulting in a rupture of the breathable air apparatus. The system my include at least one pressure gauge of the fill station to indicate any of a fill pressure of the fill station and a system pressure of the air distribution system. Further, any of a fire rated material and a fire rated assembly may enclose the distribution structure such that the distribution structure has the ability to withstand elevated temperatures for a prescribed period of time. A sleeve at least three times an outer diameter of each of a plurality of pipes of the distribution structure exterior to the fire rated material to further protect the fire rated material from any damage. Both ends of the sleeve are fitted with a fire rated material that is approved by an authority agency. Further, the system may include a robust solid casing of the distribution structure to prevent physical damage to the distribution structure potentially compromising the safety and integrity of the air distribution system.

In addition the system may include a plurality of support structures of each pipe of the distribution structure at intervals no larger than five feet to provide adequate structural support for each pipe and an another sleeve at least three times an outer diameter of a pipe of the distribution structure exterior to the robust solid casing to further protect the robust solid casing from any damage. Both ends of the another sleeve may be fitted with a fire rated material that is approved by the authority agency. Further, the system may include support structures of the pipes of the distribution structure at intervals no larger than five feet to provide adequate structural support for each pipe. In addition, the distribution structure comprises any of a stainless steel and a thermoplastic material that is compatible for use with compressed air. The system may also include an air monitoring system to automatically track and record any of impurities and contaminants in the breathable air of the air distribution system. The air monitoring system may also include an automatic shut down feature to suspend air distribution to the fill station in a case that any of an impurity and contaminant concentration exceeds a safety threshold and a pressure monitoring system to automatically track and record the system pressure of the air distribution system. In addition, the system may include a pressure switch that is electrically coupled to a fire alarm system of the building structure such that the fire alarm system is set off when the system pressure of the air distribution system is outside a safety range. The pressure switch may electrically transmit a warning signal to an emergency supervising station when the system pressure of the air distribution system is outside the safety range.

The fill station may have a physical capacity to enclose multiple breathable air apparatuses simultaneously. Further, the supply unit enclosure may include a tamper switch of the locking mechanism such that a alarm is automatically triggered and a signal is electrically coupled to any of a relevant administrative personnel of the building structure and the emergency supervising station when an intrusion of any of the supply unit and the secure chamber occurs. Further, the secure chamber may include a securing mechanism of the fill station having a locking function that is automatically actuated via a coupling mechanism with a flow switch that indicates a status of air flow to the breathable air apparatus that is fillable in the fill station. The secure chamber may be certified to be rupture containable according to approved standards.

In another aspect, a method of a building structure includes ensuring that a prescribed pressure of an emergency support system maintains within a threshold range of the prescribed pressure by including a valve of the emergency support system to prevent leakage of breathable air from the emergency support system, safeguarding a filling process of a breathable air apparatus by enclosing the breathable air apparatus in a secure chamber of a fill site of the emergency support system of the building structure to provide a safe placement to supply the breathable air to the breathable air apparatus, and maintaining the prescribed pressure of the emergency support system such that a system pressure is compatible with the breathable air apparatus through a distribution structure that is rated for use with compressed air that couples the supply unit and the fill site to transfer breathable air of the source of compressed air to the fill site.

In addition, corrosion and physical damage due to weather may be prevented by incorporating a supply unit enclosure that is weather resistant. Intrusion of the supply unit potentially compromising the safety and reliability of the breathing emergency support system may be prevented by incorporating a locking mechanism of the supply unit enclosure. Further, physical damage of various external hazards may be minimized to protect the supply unit and the fill site from any of an intrusion and damage through utilizing a robust metallic material to the supply unit enclosure.

Leakage of air may be from the emergency support system leading to a potential pressure loss of the emergency support system through utilizing any of a valve of the supply unit and the fill site. Transfer of breathable air may be discontinued from the source of compressed air to the emergency support system through utilizing a valve to the supply unit. Breathable air may be automatically released from the emergency support system when the system pressure of the emergency support system exceeds the prescribed pressure through triggering a safety relief valve of any of the supply unit and the fill site. Compatibility of the emergency support system may be ensured and the source of compressed air of an authority agency through any of a CGA connector and a RIC (rapid interventions company/crew)/UAC (universal air connection) connector of the supply unit.

In addition, a fill pressure may be adjusted to ensure that the fill pressure of the source of compressed air does not exceed the prescribed pressure of the emergency support system through a pressure regulator of the supply unit. Any of the system pressure of the emergency support system and the fill pressure of the source of compressed air may be monitored through the pressure gauge of the supply unit enclosure. Accessibility of the supply unit enclosure may be improved through providing luminescence in reduced light environments by incorporating a visible marking. A fill site may be isolated from a remaining portion of the emergency support system using an isolation valve of the fill site such that the remaining portion of the emergency support system is utilizable in an emergency situation. The isolation valve may be automatically actuated based on an air pressure sensor of the emergency support system Any of the fill pressure of the fill station and the system pressure of the emergency support system may be adjusted to ensure that the fill pressure of the fill station does not exceed the pressure rating of the breathable air apparatus through a pressure regulator of the fill site. Further, the distribution structure may be enabled to withstand elevated temperatures for a prescribed period of time using a fire rated material to encase the distribution structure. The fire rated material may be prevented from any damage by incorporating a sleeve at least three times an outer diameter of each of a plurality of pipes of the distribution structure exterior to the fire rated material. Physical damage to the distribution structure potentially compromising the safety and integrity of the emergency support system may be prevented by utilizing a robust solid casing of the distribution structure. The robust solid casing may be protected from any damage using another sleeve at least three times an outer diameter of a pipe of the distribution structure exterior to the robust solid casing.

Any of impurities and contaminants in the breathable air of the breathing emergency support system may be automatically tracked and recorded through an air monitoring system. Air distribution to the fill sites may be automatically suspended in a case that any of an impurity and contaminant concentration exceeds a safety threshold. The system pressure of the emergency support system may be tracked and recorded through a pressure monitoring system. The pressure monitoring system and the alarm system of the building structure may be electrically coupled such that the alarm system is automatically triggered through an pressure switch when the system pressure of the emergency support system is below a prescribed level. In addition, a warning signal may be electrically transmitted to an emergency supervising station when the system pressure of the emergency support system is below the prescribed level through the pressure switch.

An alarm may be automatically triggered and a signal may be electrically coupled to any of a relevant administrative personnel of the building structure and the emergency supervising station when an intrusion of the supply unit occurs through a tamper switch of the locking mechanism of the supply unit enclosure. The prescribed pressure of the emergency support system may be designated base on a municipality code that specifies a pressure rating of the breathable air apparatus that is used in an authority agency of a particular geographical location.

In yet another aspect, a building structure may include a first set of walls extending vertically and horizontally enclosing an area of land such that the area of land is in the internal region of the building structure, a second set of walls that divide the internal region of the building structure in any of a horizontal and vertical direction into rooms displaced any of a horizontally and vertically from one another, a supply unit adjacent to a particular wall of the first set of walls to facilitate delivery of breathable air from a source of compressed air to an emergency support system of the building structure, a fill station of the internal region of the building structure to provide the breathable air to a breathable air apparatus at multiple locations of the building structure, and a distribution structure that is compatible with use with compressed air that facilitates dissemination of the breathable air of the source of compressed air to multiple locations of the building structure.

The building structure may also include an air monitoring system to automatically track and record any impurities and contaminants in the breathable air of the air distribution system, an air pressure monitor that is electrically coupled to an alarm such that the alarm is set off when the system pressure of the air distribution system is outside a prescribed threshold range, and a physical enclosure of the fill station exterior to the secure chamber of the fill station that provides additional protection to the fill station from any of an elevated temperature or physical impact.

The methods, systems, and apparatuses disclosed herein may be implemented in any means for achieving various aspects, and may be executed in a form of a machine-readable medium embodying a set of instructions that, when executed by a machine, cause the machine to perform any of the operations disclosed herein. Other features will be apparent from the accompanying drawings and from the detailed description that follows.

BRIEF DESCRIPTION OF THE DRAWINGS

Example embodiments are illustrated by way of example and not limitation in the figures of the accompanying drawings, in which like references indicate similar elements and in which:

FIG. 4A is a front view of a supply unit, according to one embodiment.

FIG. 4B is a rear view of a supply unit, according to one embodiment.

Other features of the present embodiments will be apparent from the accompanying drawings and from the detailed description that follows.

DETAILED DESCRIPTION

A safety system and method having a fill station are disclosed. In the following description, for the purposes of explanation, numerous specific details are set forth in order to provide a thorough understanding of the various embodiments. It will be evident, however to one skilled in the art that the various embodiments may be practiced without these specific details.

Figure 6A:
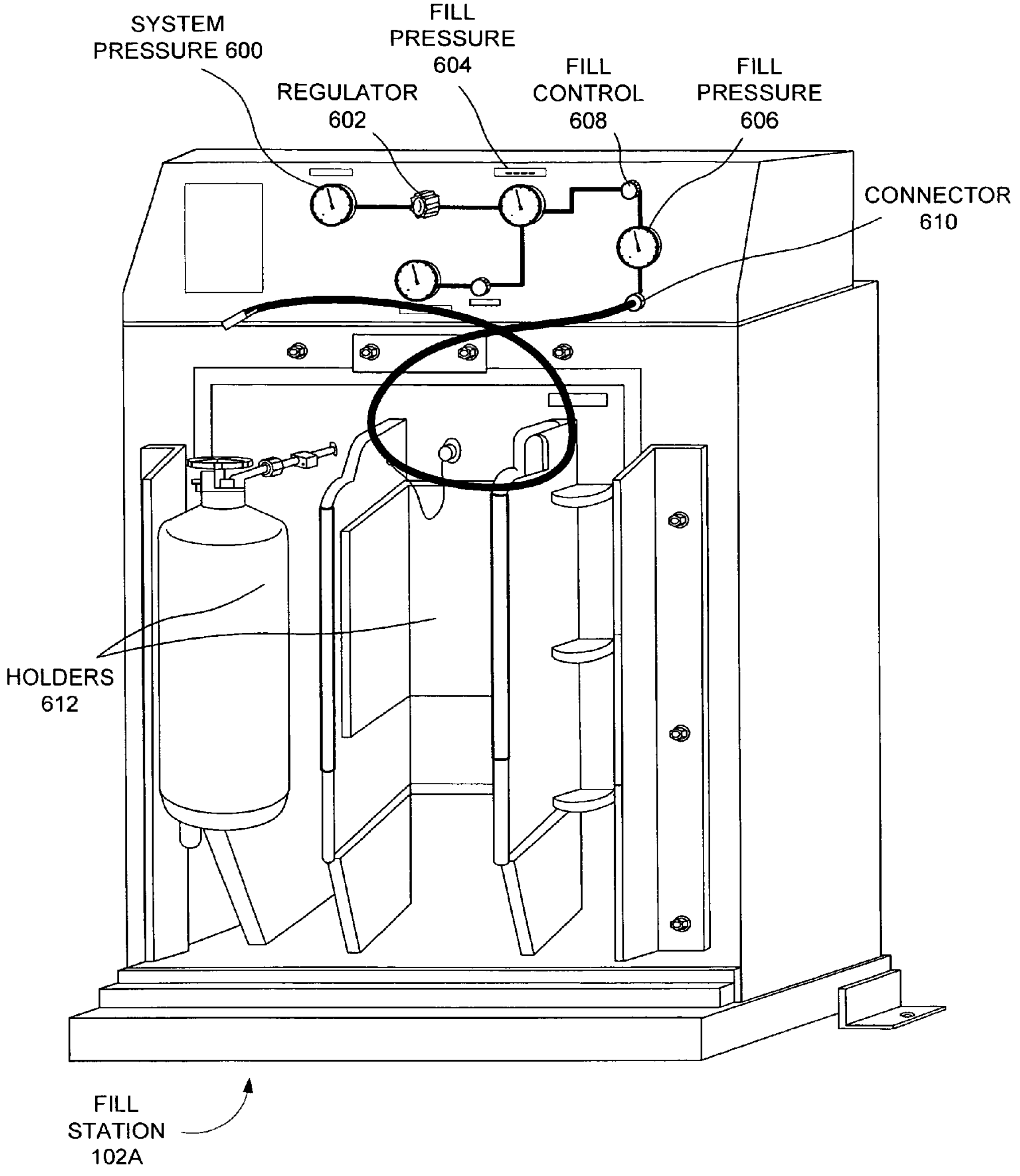
FIG. 6A is an illustration of a fill station, according to one embodiment.
Figure 6B:
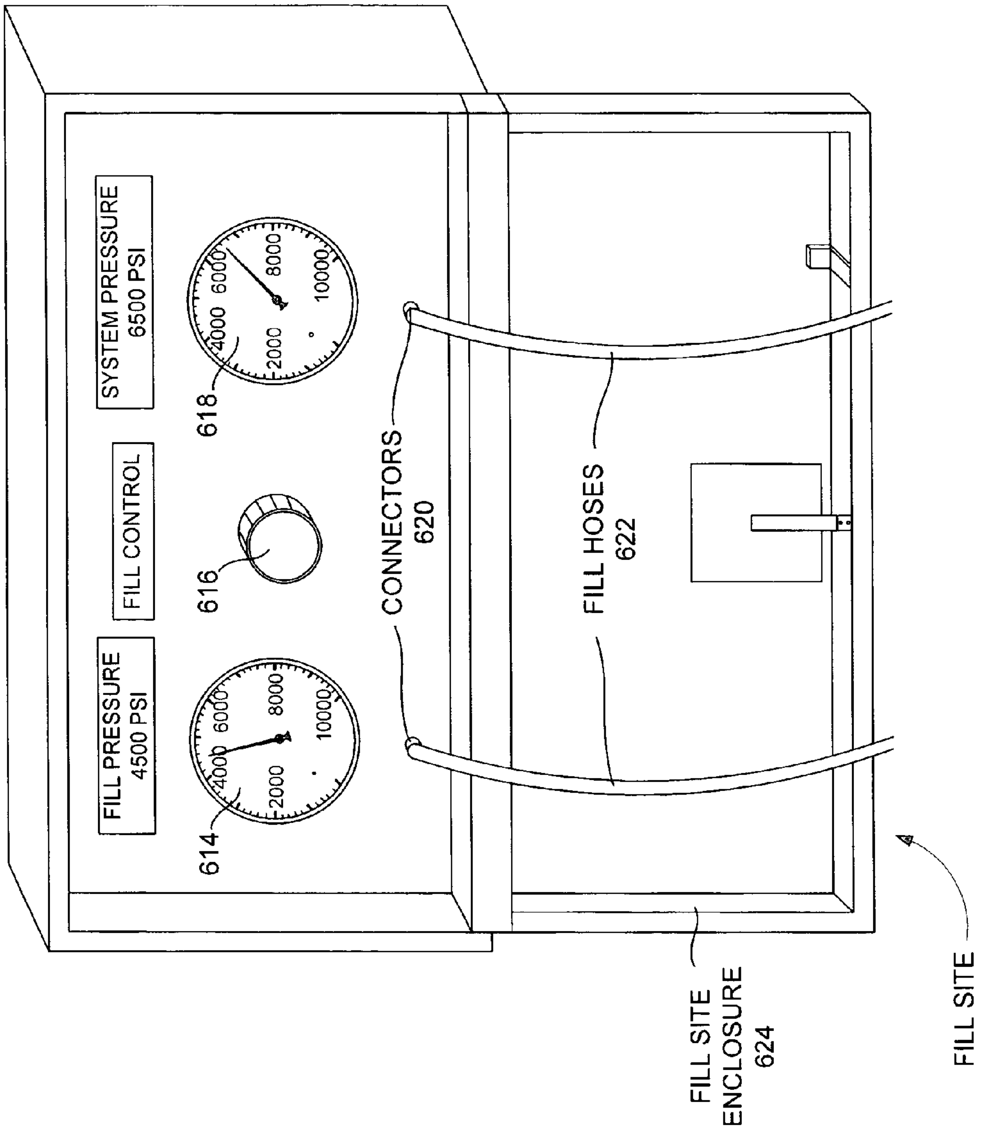
FIG. 6B is an illustration of a fill site, according to one embodiment.

In one embodiment, a safety system of a building structure includes a supply unit (e.g., a supply unit 100 of FIGS. 1-3) of a building structure to facilitate delivery of breathable air from a source of compressed air to an air distribution system (e.g., an air distribution system 150, 250, 350 of FIGS. 1-3), a valve (e.g., a valve of a series of valves 410 of FIG. 4) to prevent leakage of the breathable air from the air distribution system (e.g., the air distribution system 150, 250, 350 of FIGS. 1-3) potentially leading to loss of a system pressure, a fill site (e.g., a fill site 102B of FIG. 6B, and/or a fill station 102A of FIG. 6A) interior to the building structure to provide the breathable air to a breathable air apparatus at multiple locations of the building structure, a secure chamber housing of the fill site (e.g., the fill site 102B of FIG. 6B, and/or the fill station 102A of FIG. 6A) as a safety shield that confines a possible rupture of an over-pressurized breathable air apparatus within the secure chamber, and/or a distribution structure (e.g., a distribution structure 104 of FIGS. 1-3) that is compatible with use with compressed air that facilitates dissemination of the breathable air of the source of compressed air to multiple locations of the building structure, In another embodiment, a method may include ensuring that a prescribed pressure of the emergency support system (e.g., the air distribution system 150, 250, 350 of FIGS. 1-3) maintains within a threshold range of the prescribed pressure by including a valve of the emergency support system to prevent leakage of breathable air from the emergency support system (e.g., the air distribution system 150, 250, 350 of FIGS. 1-3), safeguarding a filling process of a breathable air apparatus by enclosing the breathable air apparatus in a secure chamber of a fill site (e.g., a fill site 102B of FIG. 6B, and/or a fill station 102A of FIG. 6A) of the emergency support system (e.g., the air distribution system 150, 250, 350 of FIGS. 1-3) of the building structure to provide a safe placement to supply the breathable air to the breathable air apparatus, and/or maintaining the prescribed pressure of the emergency support system (e.g., the air distribution system 150, 250, 350 of FIGS. 1-3) such that a system pressure is compatible with the breathable air apparatus through a distribution structure that is rated for use with compressed air that couples the supply unit and the fill site (e.g., a fill site 102B of FIG. 6B, and/or a fill station 102A of FIG. 6A) to transfer breathable air of the source of compressed air to the fill site (e.g., a fill site 102B of FIG. 6B, and/or a fill station 102A of FIG. 6A).

In yet another embodiment, a building structure (e.g., a horizontal building structure such as a shopping mall, IKEA, Home Depot, a vertical building structure such as a high rise building, a mid rise building, and/or a low rise building, a mine, a subway, and/or a tunnel, etc.) includes a first set of walls extending vertically and horizontally enclosing an area of land such that the area of land is in the internal region of the building structure, a second set of walls that divide the internal region of the building structure in any of a horizontal and vertical direction into rooms displaced any of a horizontally and vertically from one another, a supply unit (e.g., the supply unit 100 of FIGS. 1-3) adjacent to a particular wall of the first set of walls to facilitate delivery of breathable air from a source of compressed air to an emergency support system (e.g., the air distribution system 150, 250, 350 of FIGS. 1-3) of the building structure, a fill site (e.g., the fill site 102B of FIG. 6B, and/or the fill station 102A of FIG. 6A) of the internal region of the building structure to provide the breathable air to a breathable air apparatus at multiple locations of the building structure, a secure chamber housing the fill site (e.g., the fill site 102B of FIG. 6B, and/or the fill station 102A of FIG. 6A) as a safety shield that confines a possible rupture of an over-pressurized breathable air apparatus within the secure chamber, and/or a distribution structure (e.g., a distribution structure 104 of FIGS. 1-3) that is compatible with use with compressed air that facilitates dissemination of the breathable air of the source of compressed air to multiple locations of the building structure.

Figure 1:
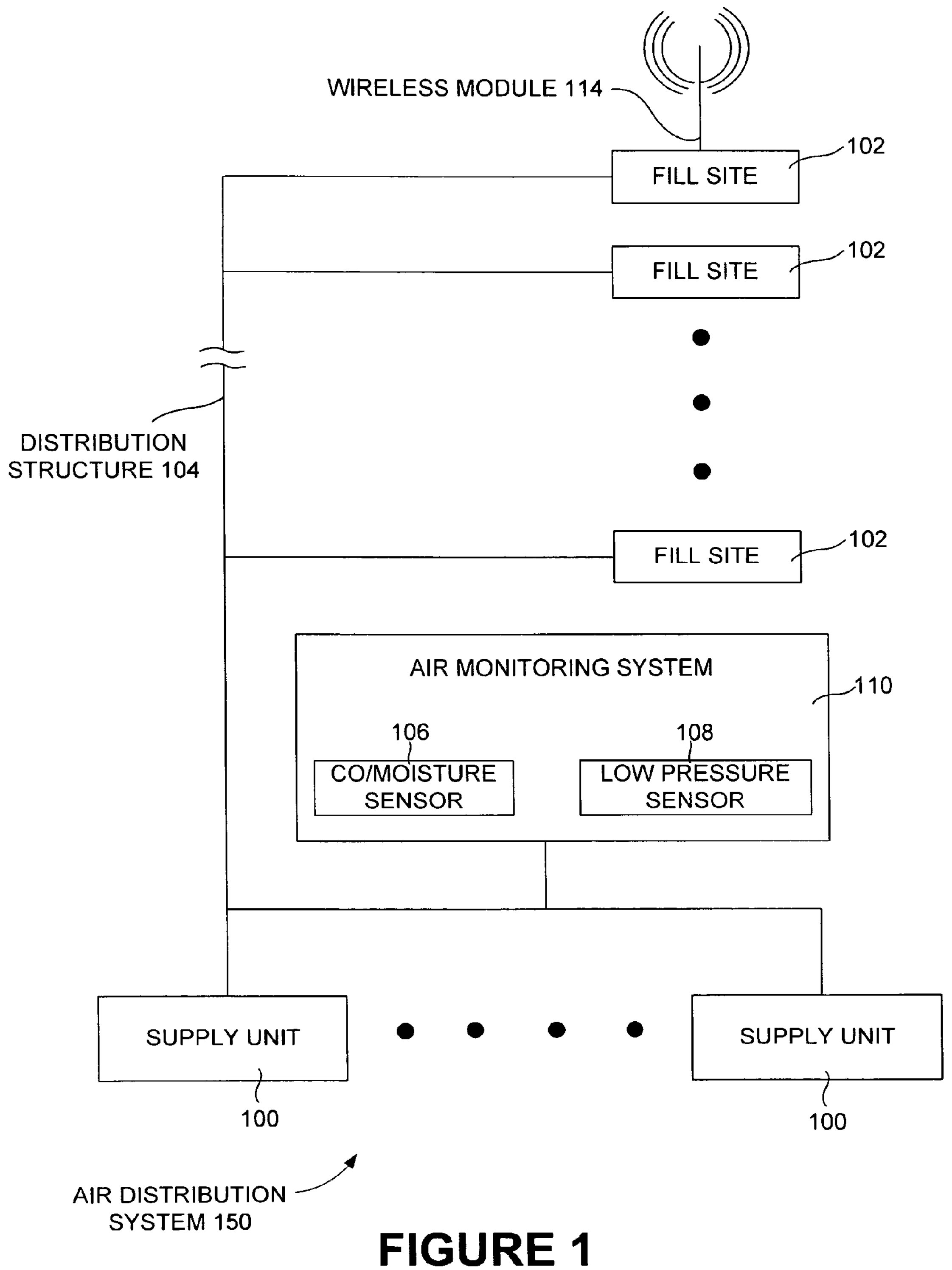
FIG. 1 is a diagram of an air distribution system in a building structure, according to one embodiment.

FIG. 1 is a diagram of an air distribution system 150 in a building structure, according to one embodiment. The air distribution system 150 may include any number of supply units 100, any number of fill sites 102 (e.g., a fill panel and/or a fill station, etc.) that are coupled to the rest of the air distribution system 150 through a distribution structure 104. The air distribution system 150 may also include a air monitoring system 110 having a CO/Moisture sensor 106 and a pressure sensor 108. The supply unit 100 may be placed at a number of locations exterior to the building structure (e.g., a horizontal building structure such as a shopping mall, IKEA, Home Depot, a vertical building structure such as a high rise building, a mid rise building, and/or a low rise building, a mine, a subway, and/or a tunnel, etc.) to allow ease of access by a source of compressed air and/or to expedite supplying the air distribution system 150 with breathable air. The supply units 100 may also be placed at locations that are substantially free of traffic (e.g., parked cars, vehicle movement, and/or human traffic, etc.) to decrease potential obstruction that may be present in an emergency situation (e.g., a building fire, a chemical attack, terror attack, subway accident, mine collapse, and/or a biological agent attack, etc.).

The fill site 102 may also be placed at a number of locations of the building structure (e.g., a horizontal building structure such as a shopping mall, IKEA, Home Depot, a vertical building structure such as a high rise building, a mid rise building, and/or a low rise building, a mine, a subway, and/or a tunnel, etc.) to provide multiple access points to breathable air in the building structure. The building structure may have any number of fill sites 102 (e.g., a fill panel and/or a fill station, etc.) on each floor and/or have fill sites 102 (e.g., a fill panel and/or a fill station, etc.) on different floors. Each fill site 102 may be sequentially coupled to one another and to the supply units 100 through the distribution structure 104. The distribution structure 104 may include any number of pipes to expand an air carrying capacity of the air distribution system 150 such that breathable air may be replenished at a higher rate. In addition, the fill site 102 may include wireless capabilities (e.g., a wireless module 114) for communication with remote entities (e.g., the supply unit 100, building administration, and/or an authority agency, etc.).

The air monitoring system 110 may contain multiple sensors such as the CO/moisture sensor 106 and the pressure sensor 108 to track air quality of the breathable air in the air distribution system 150. Since emergency personnel (e.g., a fire fighter, a SWAT team, a law enforcer, and/or a medical worker, etc.) depend on the breathable air distributed via the air distribution system 150, it is crucial that air quality of the breathable air be constantly maintained. The air monitoring system 110 may also include other sensors that detect other hazardous substances (e.g., benzene, acetamide, acrylic acid, asbestos, mercury, phosphorous, propylene oxide, etc.) that may contaminate the breathable air.

In one embodiment, the distribution structure 104 may be compatible with use with compressed air facilitates dissemination of the breathable air of the source of compressed air to multiple locations of the building structure. A fire rated material may encase the distribution structure 104 such that the distribution structure has the ability to withstand elevated temperatures for a period of time. The pipes of the distribution structure 104 may include a sleeve exterior to the fire rated material to further protect the fire rated material from any damage. Both ends of the sleeve may be fitted with a fire rated material that is approved by an authority agency. In addition, the distribution structure 104 may include a robust solid casing to prevent physical damage to the distribution structure potentially compromising the safety and integrity of the air distribution system.

The distribution structure 104 may include support structures at intervals no larger than five feet to provide adequate structural support for each pipe of the distribution structure 104. The pipes and the fittings of the distribution structure 104 may include any of a stainless steel and a thermoplastic material that is compatible for use with compressed air.

In another embodiment, the air distribution system may include an air monitoring system (e.g., the air monitoring system 110) to automatically track and record any impurities and contaminants in the breathable air of the air distribution system. The air monitoring system (e.g., the air monitoring system 110) may have an automatic shut down feature to suspend air distribution to the fill sites 102 in a case that any of an impurity and contaminant concentration exceeds a safety threshold. For example, a pressure monitoring system (e.g., the pressure sensor 108) may automatically track and record the system pressure of the air distribution system. Further, a pressure switch may be electrically coupled to a alarm system such that the fire alarm system is set off when the system pressure of the air distribution system is outside a safety range.

Figure 2:
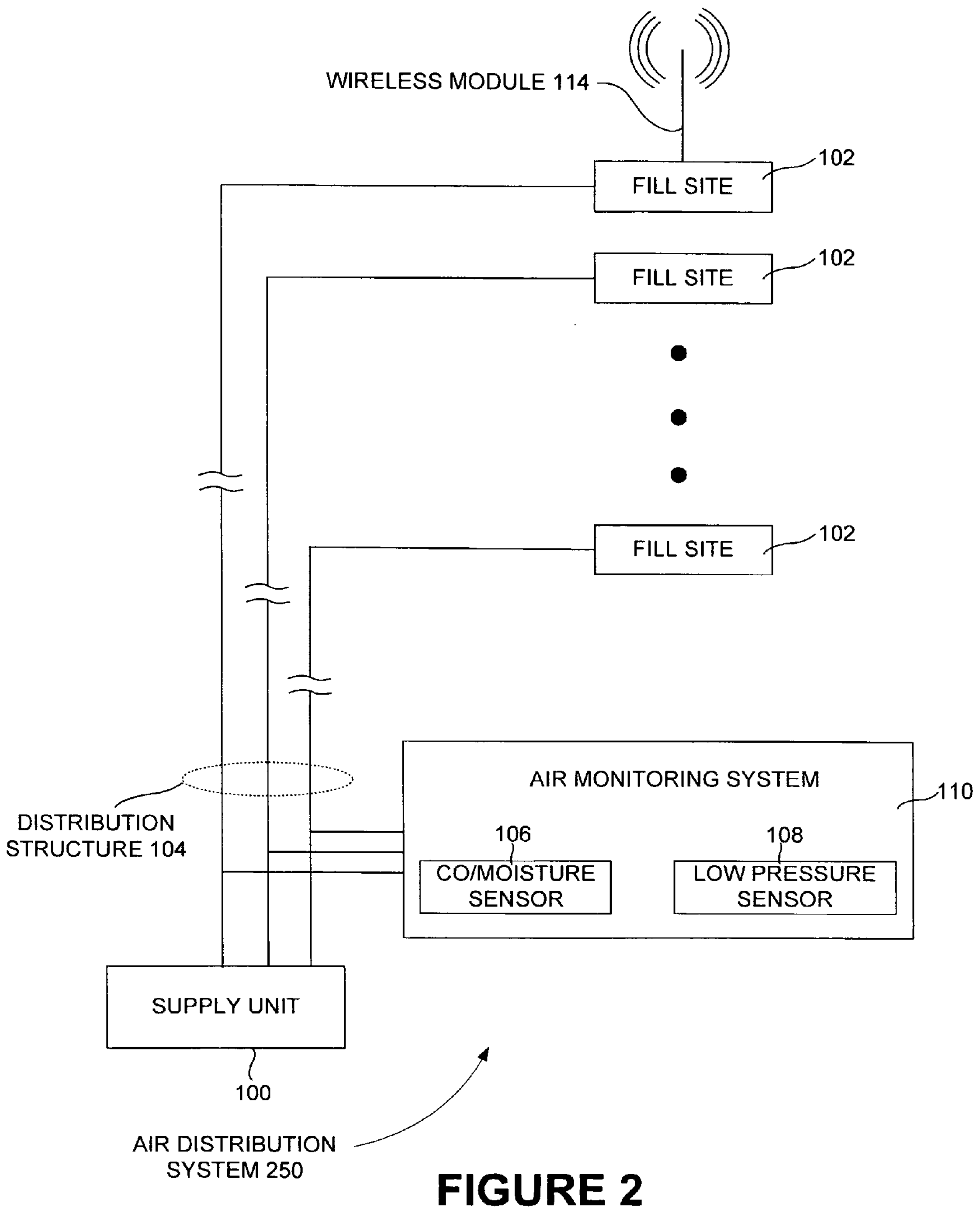
FIG. 2 is another diagram of an air distribution system in a building structure, according to one embodiment.

FIG. 2 is another diagram of an air distribution system 250 in a building structure, according to one embodiment. The air distribution system 250 may include any number of supply units 100, any number of fill sites 102 (e.g., a fill panel and/or a fill station, etc.) that are coupled to the rest of the air distribution system 150 through a distribution structure 104. The air distribution system 150 may also include a air monitoring system 110 having a CO/Moisture sensor 106 and a pressure sensor 108. In the air distribution system 250, the distribution structure 104 may individually couple each fill site 102 (e.g., a fill panel and/or a fill station, etc.) to a supply unit 100. Individual coupling may be advantageous in that in the case one pipe of the distribution structure 104 becomes inoperable the other pipes can still deliver air to the fill sites 102 (e.g., a fill panel and/or a fill station, etc.). The other system components (e.g., the fill site 102, the supply unit 100, and the air monitoring system 110 were described in detail in the previous section).

Figure 3:
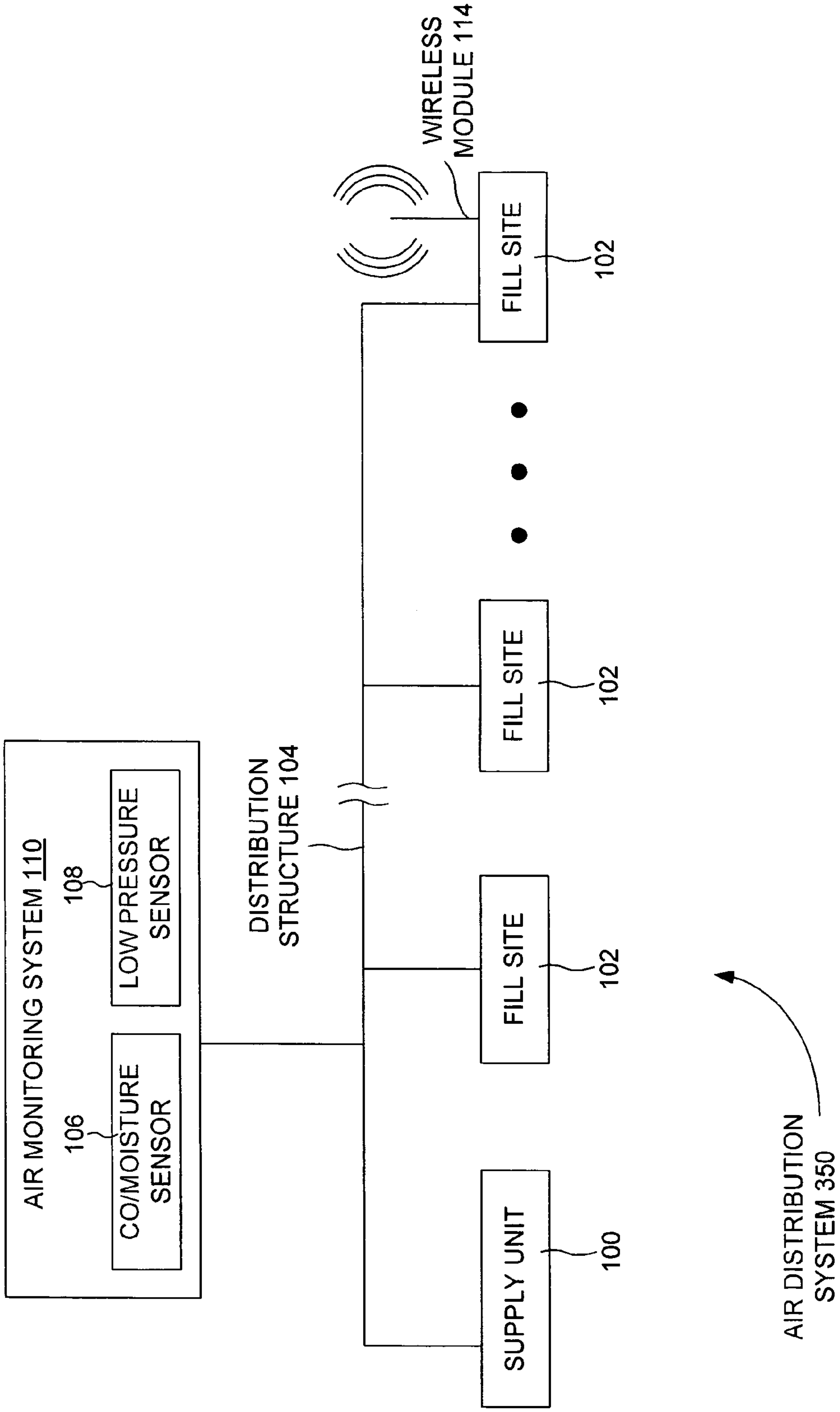
FIG. 3 is a diagram of an air distribution system in a building structure having fill sites located horizontally from one another, according to one embodiment.

FIG. 3 is a diagram of an air distribution system 350 in a building structure having fill sites 102 (e.g., a fill panel and/or a fill station, etc.) located horizontally from one another, according to one embodiment.

The air distribution system 350 may include any number of supply units 100, any number of fill sites 102 (e.g., a fill panel and/or a fill station, etc.) that are coupled to the rest of the air distribution system 150 through a distribution structure 104. The air distribution system 150 may also include a air monitoring system 110 having a CO/Moisture sensor 106 and a pressure sensor 108. In the air distribution system 250, the distribution structure 104 may sequentially couple each fill site 102 (e.g., a fill panel and/or a fill station, etc.) displaced predominantly horizontally from a supply unit 100. Each air distribution system (e.g., the air distribution system 150, 250, 350) may be used in conjunction with one another depending on the particular architectural style of the building structure in a manner that provides most efficient access to the breathable air of the air distribution system reliably. The other system components (e.g., the fill site 102, the supply unit 100, and the air monitoring system 110 were described in detail in the previous section).

FIG. 4A is a front view of a supply unit 100, according to one embodiment.

The supply unit 100 provides accessibility of a source of compressed air to supply air to an air distribution system (e.g., an air distribution system 150, 250, and/or 350). The supply unit may include a fill pressure indicator 400, a fill control knob 402, a system pressure indicator 404, and/or a connector 406. The fill pressure indicator 400 may indicate the pressure level at which breathable air is being delivered by the source of compressed air to the air distribution system (e.g., an air distribution system 150, 250, and/or 350 of FIGS. 1-3). The system pressure indicator 404 may indicate the current pressure level of the breathable air in the air distribution system. The fill control knob 402 may be used to control the fill pressure such that the fill pressure does not exceed a safety threshold that the air distribution system is designed for. The connector 406 may be a CGA connector that is compatible with an air outlet of the source of compressed air of various emergency agencies (e.g., fire station, law enforcement agency, medical provider, and/or SWAT team, etc.). The connector 406 of the supply unit 100 may facilitate a connection with the source of compressed air through ensuring compatibility of the supply unit 100 with the source of compressed air.

The supply unit 100 may include an adjustable pressure regulator of the supply unit 100 that is used to adjust a fill pressure of the source of compressed air to ensure that the fill pressure does not exceed the design pressure of the air distribution system. Further, the supply unit may also include at least one pressure gauge of the supply unit enclosure to indicate any of the system pressure (e.g., the system pressure indicator 404) of the air distribution system and the fill pressure (e.g., the fill pressure indicator 400) of the source of compressed air.

FIG. 4B is a rear view of a supply unit 100, according to one embodiment.

The supply unit also includes a series of valves 410 (e.g., a valve, an isolation valve, and/or a safety relief valve, etc.) to further ensure that system pressure is maintained within a safety threshold of the design pressure of the air distribution system.

The supply unit 100 of a building structure may facilitate delivery of breathable air from a source of compressed air to an air distribution system of the building structure. The supply unit 100 includes the series of valves 410 (e.g., the valve, and/or the safety relief valve, etc.) to prevent a leakage of the breathable air from the air distribution system potentially leading to loss of a system pressure. For example, the supply unit 100 may include the valve of the series of valves 410 to automatically suspend transfer of breathable air from the source of compressed air to the air distribution system when useful. The safety relief valve of the supply unit 100 and/or the fill site 102 may release breathable air when a system pressure of the air distribution system exceeds a threshold value beyond the design pressure to ensure reliability of the air distribution system through maintaining the system pressure such that it is within a pressure rating of each component of the air distribution system.

Figure 5:
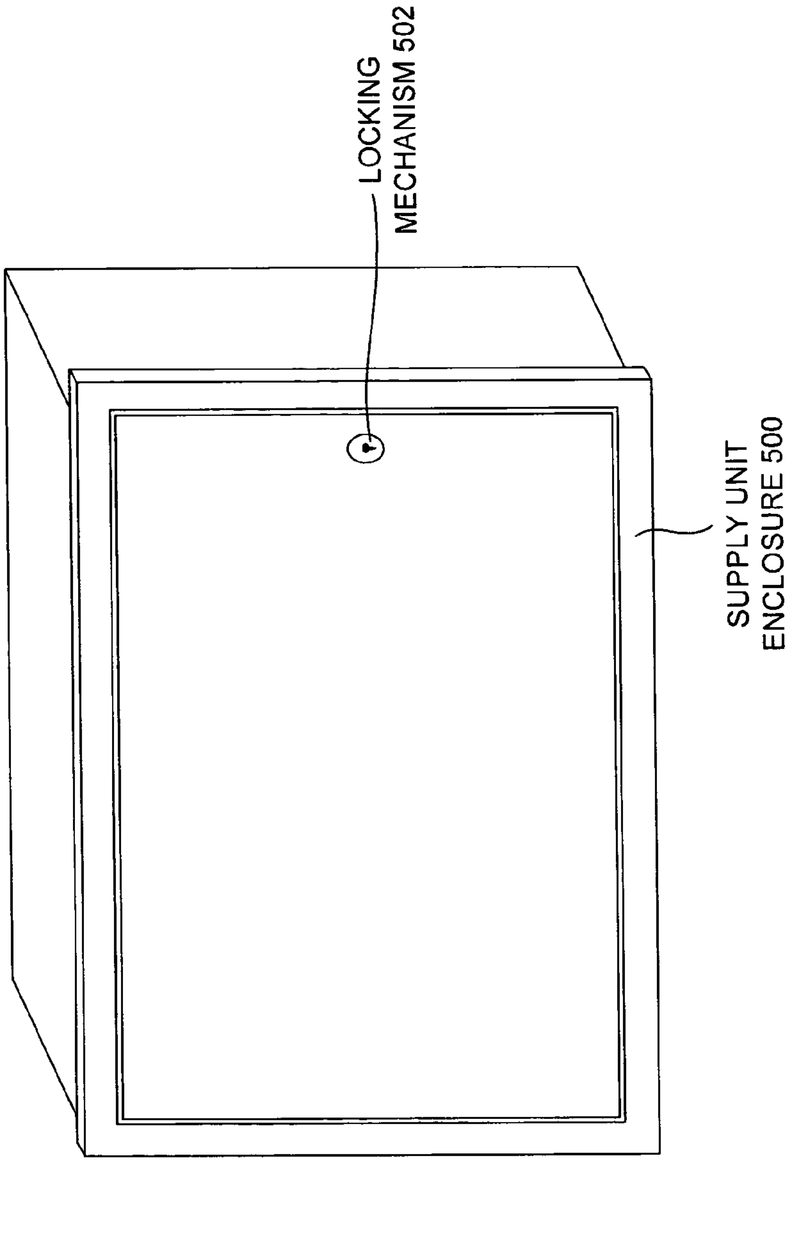
FIG. 5 is an illustration of a supply unit enclosure, according to one embodiment.

FIG. 5 is an illustration of a supply unit enclosure 500, according to one embodiment.

The supply unit enclosure 500 may include a locking mechanism 502 to secure the supply unit 100 from unauthorized access. Further, the supply unit enclosure 500 may also contain fire rated material such that the supply unit 100 is able to withstand burning elevated temperatures.

The supply unit enclosure 500 encompassing the supply unit 100 may have any of a weather resistant feature, ultra-violet and infrared solar radiation resistant feature to prevent corrosion and physical damage. The locking mechanism 502 may secure the supply unit from intrusions that potentially compromise safety and reliability of the air distribution system. In addition, the supply unit enclosure 500 may include a robust metallic material of the supply unit enclosure 500 to minimize a physical damage due to various hazards to protect the supply unit 100 from any of an intrusion and damage. The robust metallic material may be at least substantially 18 gauge carbon steel. The supply unit enclosure 500 may include a visible marking to provide luminescence in a reduced light environment. The locking mechanism 502 may also include a tamper switch such that a alarm is automatically triggered and a signal is electrically coupled to any of a relevant administrative personnel of the building structure and the emergency supervising station when an intrusion of any of the supply unit and the secure chamber occurs.

FIG. 6A is an illustration of a fill station 102A, according to one embodiment.

The fill station 102A may be a type of fill site 102 of FIG. 1. The fill station 102A may include a system pressure indicator 600, a regulator 602, a fill pressure indicator 604, another fill pressure indicator 606, and/or fill control knob 608. The fill station 102A may also include a RIC (rapid interventions company/crew)/UAC (universal air connection) connector 610 and multiple breathable air apparatus holders 612 used to supply air from the air distribution system. The fill pressure indicator 604 may indicate the pressure level at which breathable air is being delivered by the source of compressed air to the air distribution system (e.g., an air distribution system 150,250, and/or 350 of FIGS. 1-3). The system pressure indicator 600 may indicate the current pressure level of the breathable air in the air distribution system. The fill control knob 608 may be used to control the fill pressure such that the fill pressure does not exceed a safety threshold that the air distribution system is designed for. The RIC (rapid interventions company/crew)/UAC (universal air connection) connector 610 may facilitate direct coupling to emergency equipment to supply breathable air through a hose that is connected to the RIC (rapid interventions company/crew)/UAC (universal air connection) connector 610. In essence, precious time may be saved because the emergency personnel may not need to spend the time to remove the emergency equipment from their rescue attire before they can be supplied with breathable air. Further, the RICNAC connector 610 may also directly couple to a face-piece of a respirator to supply breathable air.

The multiple breathable air apparatus holders 612 can hold multiple compressed air cylinders to be filled simultaneously. In addition, the multiple breathable air apparatus holders 612 can be rotated such that additional compressed air cylinders may be loaded while the multiple compressed air cylinders are filled inside the fill station 102A. The fill station 102A may be a rupture containment chamber such that over-pressurized compressed air cylinders are shielded and contained to prevent injuries.

In one embodiment, the fill station 102A interior to the building structure may provide the breathable air to a breathable air apparatus at multiple locations of the building structure. A secure chamber of the fill station 102A may be a safety shield that confines a possible rupture of an over-pressurized breathable air apparatus within the secure chamber. The fill station 102A may include a valve to prevent leakage of air from the air distribution system potentially leading to pressure loss of the air distribution system through ensuring that the system pressure is maintained within a threshold range of the design pressure to reliably fill the breathable air apparatus. An isolation valve may be included to isolate a breathable fill station from a remaining portion of the air distribution system.

The isolation valve may be automatically actuated based on an air pressure sensor of the air distribution system. The fill station 102A may include at least one pressure regulator to adjust a fill pressure to fill the breathable air apparatus and to ensure that the fill pressure does not exceed the pressure rating of the breathable air apparatus potentially resulting in a rupture of the breathable air apparatus. The fill station 102A may include at least one pressure gauge to indicate any of a fill pressure (e.g., the fill pressure indicator 604,606) of the fill station and a system pressure (e.g., the system pressure indicator 600) of the air distribution system. In one embodiment, the fill station 102A may have a physical capacity to enclose at least one breathable air apparatus and may include a RIC (rapid interventions company/crew)/UAC (universal air connection) connector to facilitate a filling of the breathable air apparatus. The fill station may also include a securing mechanism of the secure chamber of the fill station having a locking function is automatically actuated via a coupling mechanism with a flow switch that indicates a status of air flow to the breathable air apparatus that is fillable in the fill station.

FIG. 6B is an illustration of a fill site 102B, according to one embodiment.

The fill site 102B (e.g., a fill panel) includes a fill pressure indicator 614 (e.g., pressure gauge), a fill control knob 616 (e.g., pressure regulator), a system pressure indicator 618, a number of connector 620 (e.g., a RIC (rapid interventions company/crew)/UAC (universal air connection) connector), and or fill hoses 622. The fill site 102B may also include a locking mechanism of a fill site enclosure 624 (e.g., a fill panel enclosure) to secure the fill panel from intrusions that potentially compromise safety and reliability of the air distribution system. The system pressure indicator 618 may indicate the current pressure level of the breathable air in the air distribution system. The fill control knob 616 (e.g., pressure regulator) may be used to adjust the fill pressure such that the fill pressure does not exceed a safety threshold that the air distribution system is designed for.

The connector 620 may facilitate direct coupling to emergency equipment to supply breathable air through a hose that is connected to the connector 620. In essence, precious time may be saved because the emergency personnel may not need to spend the time to remove the emergency equipment from their rescue attire before they can be supplied with breathable air. Further, the connector 620 connected with the fill hoses 622 may also directly couple to a face-piece of a respirator to supply breathable air to either emergency personnel (e.g., a fire fighter, a SWAT team, a law enforcer, and/or a medical worker, etc.) and/or stranded survivors in need of breathing assistance. Each of the fill hoses 622 may have different pressure rating of the fill site 102B is couple-able to any of a self-contained breathable air apparatus and respiratory mask having a compatible RIC (rapid interventions company/crew)/UAC (universal air connection) connector. The fill panel enclosure may include a visible marking to provide luminescence in a reduced light environment.

The fill site 102B interior to the building structure may have a RIC (rapid interventions company/crew)/UAC (universal air connection) connector (e.g., the connector 620) to fill a breathable air apparatus to expedite a breathable air extraction process from the air distribution system and to provide the breathable air to the breathable air apparatus at multiple locations of the building structure. The fill site 102B may include a safety relief valve set to have an open pressure of at most approximately 10% more than a design pressure of the air distribution system to ensure reliability of the air distribution system through maintaining the system pressure such that it is within a threshold range of a pressure rating of each component of the air distribution system. The fill site enclosure 624 may comprise of at least 18 gauge carbon steel to minimize physical damage of various naturally occurring and man imposed hazards through protecting the fill panel from any of an intrusion and damage. The fill site 102B may include an isolation valve to isolate a damaged fill panel from a remaining operable portion of the air distribution system.

Figure 7B:
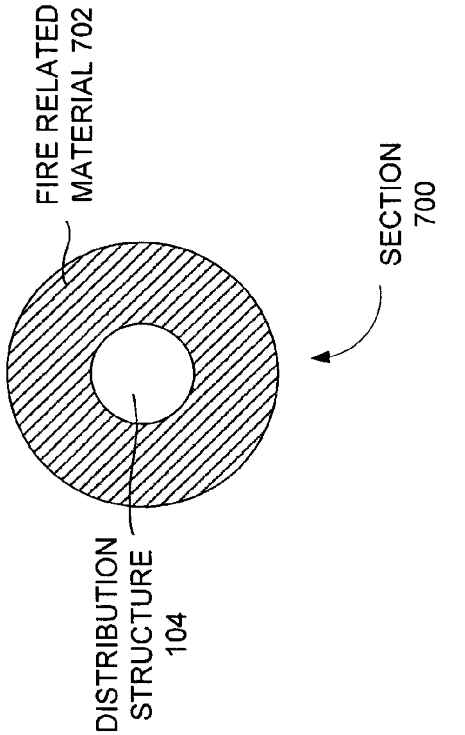
FIG. 7B is a cross sectional view of a distribution structure embedded in a fire rated material, according to one embodiment.
Figure 7A:
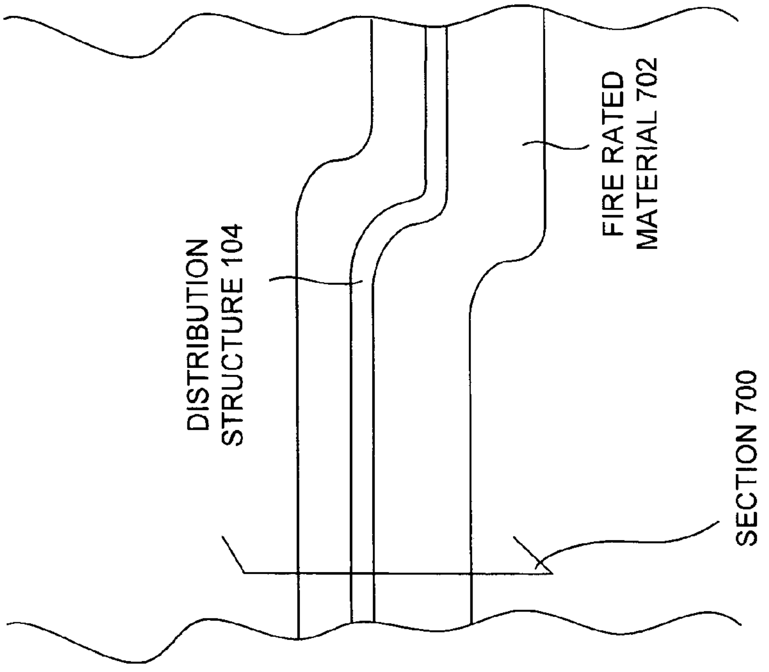
FIG. 7A is a diagrammatic view of a distribution structure embedded in a fire rated material, according to one embodiment.

FIG. 7A is a diagrammatic view of a distribution structure 104 embedded in a fire rated material, according to one embodiment.

The distribution structure 104 may be enclosed in the fire rated material 702. The fire rated material may prevent the distribution structure 104 from damage in a fire such that an air distribution system (e.g., the air distribution system 150, 250, 350 of FIGS. 1-3) may be operational for a longer time period in an emergency situation (e.g., a building fire, a chemical attack, terror attack, subway accident, mine collapse, and/or a biological agent attack, etc.). Section 700 is a cross section of the distribution structure 104 embedded in the fire rated material 702.

FIG. 7B is a cross sectional view 700 of a piping structure embedded in a fire rated material, according to one embodiment.

Section 700 is a cross section of the distribution structure 104 embedded in the fire rated material 702.

Figure 8:
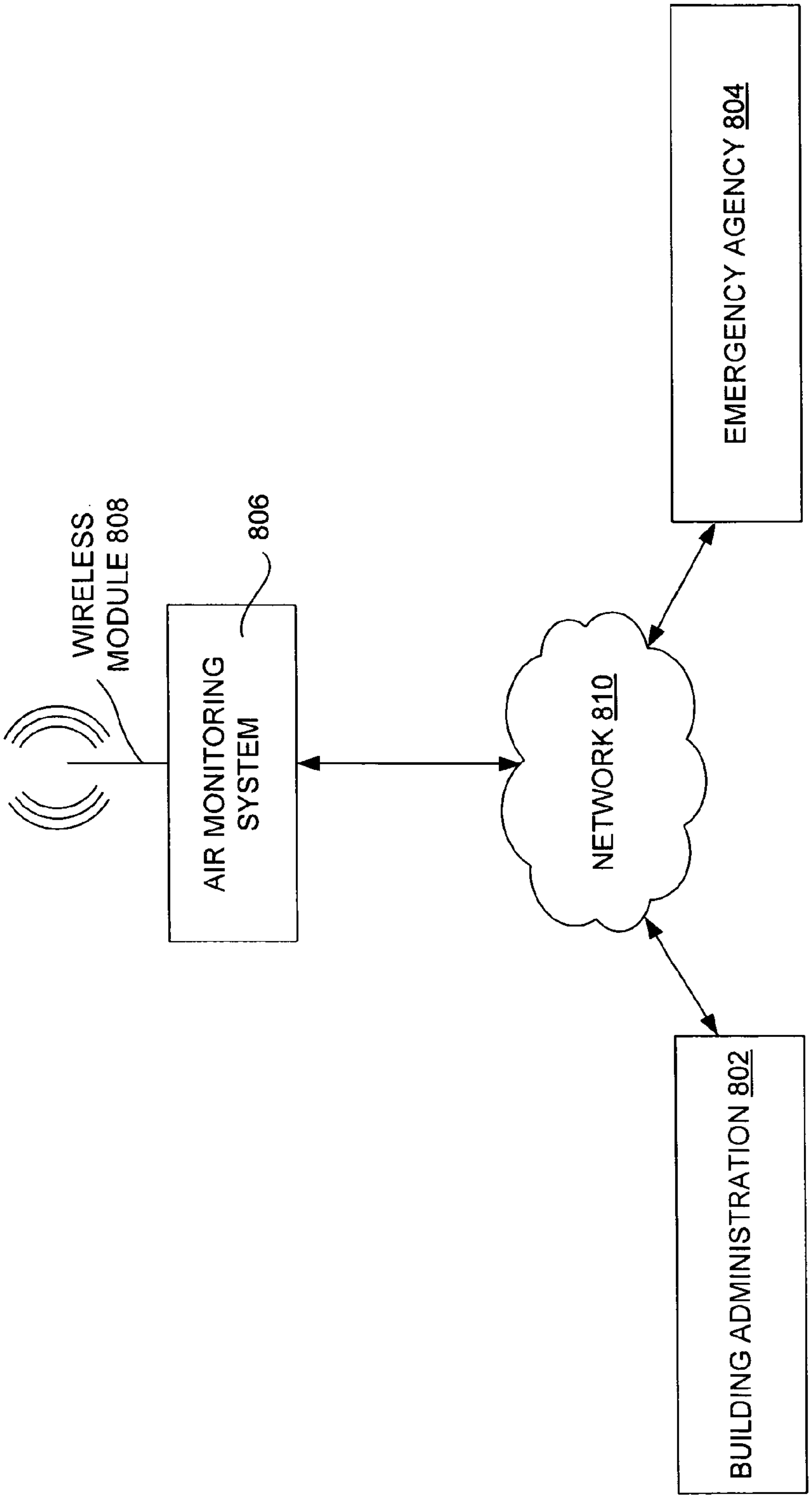
FIG. 8 is a network view of a air monitoring system that communicates building administration and an authority agency, according to one embodiment.

FIG. 8 is a network view of a air monitoring system 806 with a wireless module 808 that communicates with a building administration 802 and an authority agency 804 through a network 810, according to one embodiment.

The air monitoring system 806 may include various sensors (e.g., CO/moisture sensor 106 of FIG. 1, pressure sensor 108 of FIG. 1, and/or hazardous substance sensor, etc.) and/or status indicators regarding system readiness information (e.g., system pressure, in use, not in use, operational status, fill site usage status, fill site operational status, etc.). The air monitoring system 806 may communicate sensor readings to a building administration 802 (e.g., building management, security, and/or custodial services, etc.) such that proper maintenance measures may be taken. The air monitoring system 806 may also send alerting signals as a reminder for regular system inspection and maintenance to the building administration 802 through the network 810. The air monitoring system 806 may also communicate sensor readings to an authority agency 804 (e.g., a police station, a fire station, and/or a hospital, etc.).

Figure 9:
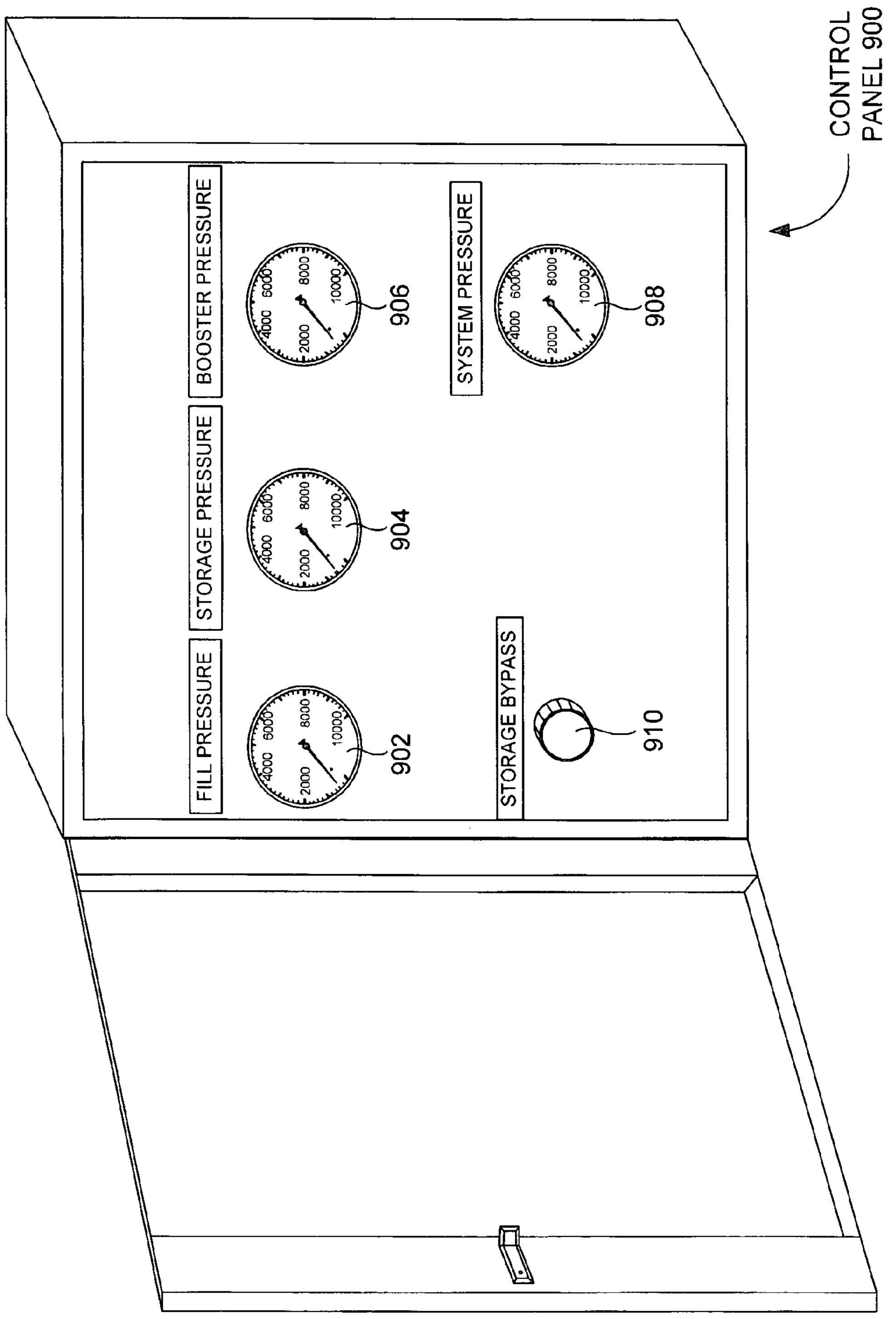
FIG. 9 is a front view of a control panel of an air storage sub-system, according to one embodiment.

FIG. 9 is a front view of a control panel 900 of a air storage sub-system 1050, according to one embodiment.

The control panel 900 includes a fill pressure indicator 902, a storage pressure indicator 904, a booster pressure indicator 906, a system pressure indicator 908 and/or a storage bypass 910. The fill pressure indicator 902 may indicate the pressure level at which breathable air is being delivered by the source of compressed air to the air distribution system (e.g., an air distribution system 150, 250, and/or 350 of FIGS. 1-3). The storage pressure indicator 904 may display the pressure level of air storage tanks in the air storage sub-system 1050. The booster pressure indicator may display the pressure level of a booster cylinder. The system pressure indicator 908 may indicate the current pressure level of the breathable air in the air distribution system. Air may be directly supplied to the air distribution system (e.g., an air distribution system 150, 250, and/or 350 of FIGS. 1-3) through the storage bypass 910.

Figure 10:
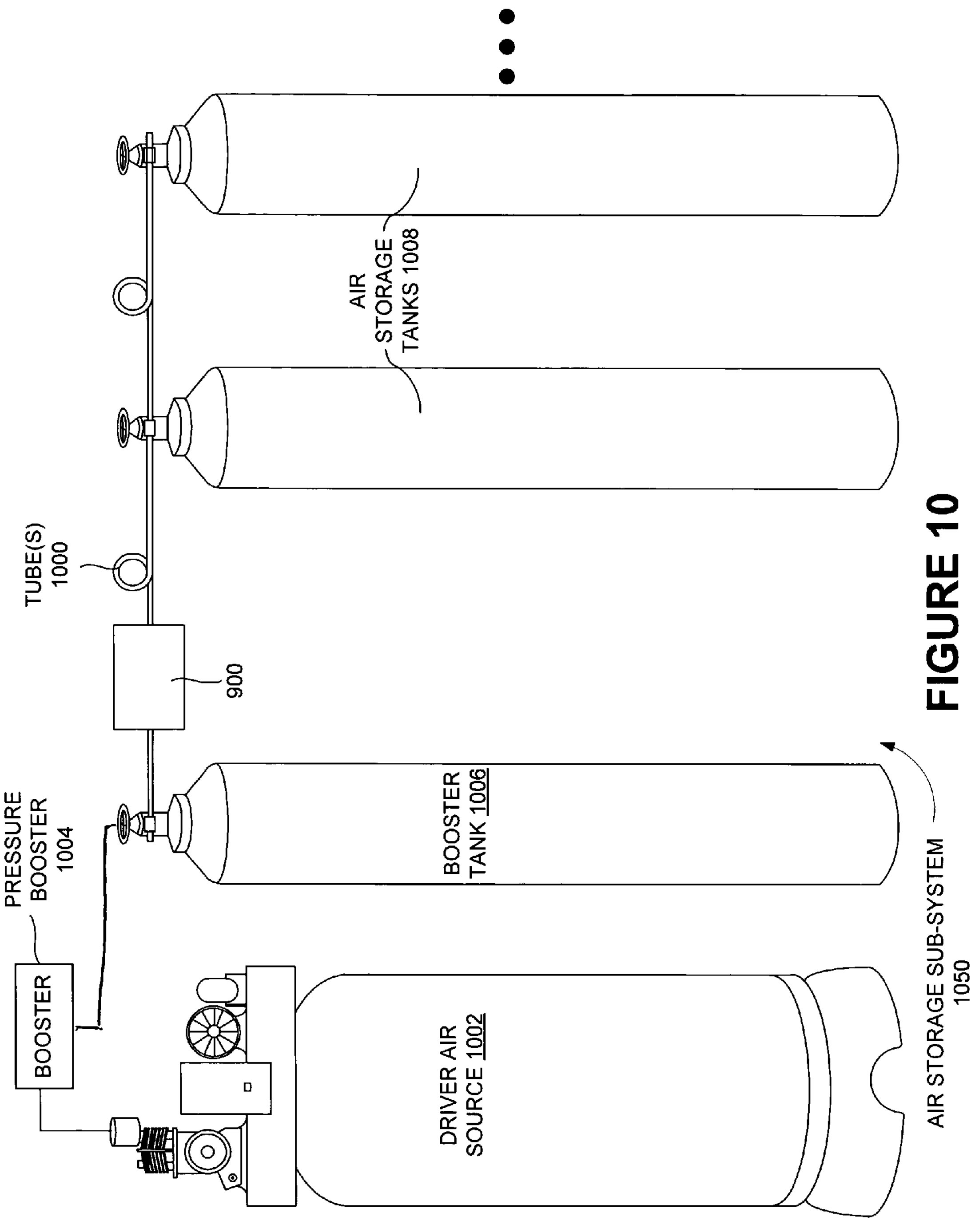
FIG. 10 is an illustration of an air storage sub-system, according to one embodiment.

FIG. 10 is an illustration of a air storage sub-system 1050, according to one embodiment.

The air storage sub-system 1050 may include a control panel 900, tubes 1000, a driver air source 1002, a pressure booster 1004, a booster tank 1006, and/or any number of air storage tanks 1008. The control panel 900 may provide status information regarding the various components of the air storage sub-system 1050. The tubes 1000 may couple each air storage tank 1008 to one another in a looped configuration to increase robustness of the tubes 1000. The driver air source 1002 may be used to pneumatically drive the pressure booster 1004 to maintain a higher pressure of the air distribution system such that a breathable air apparatus is reliably filled. The booster tank 1006 may store air at a higher pressure than the air stored in the air storage tanks 1008 to ensure that the air distribution system can be supplied with air that is sufficiently pressurized to fill a breathable air apparatus.

In one embodiment, the air storage sub-system 1050 may include an air storage tanks 1008 to provide a storage of air that is dispersible to multiple locations of the building structure. The number of air storage tanks 1008 of the air storage sub-system 1050 may be coupled to each other through tubes 1000 having a looped configuration to increase robustness of the tubes 1000 through preventing breakage due to stress. In addition, a booster tank (e.g., the booster tank 1006) of the air storage sub-system 1050 may be coupled to the plurality of air storage tanks to store compressed air of a higher pressure than the compressed air that is stored in the air storage tank 1008. A driver air source 1002 of the air storage sub-system 1050 may be coupled to a pressure booster (e.g., the pressure booster 1004) to pneumatically drive a piston of the pressure booster (e.g., the pressure booster 1004) to maintain a higher pressure of the air distribution system such that a breathable air apparatus is reliably filled.

Further, the driving air source may enable the breathable air to be optimally supplied to the building structure through allowing the breathable air to be isolated from driving the pressure booster 1004. The air storage sub-system 1050 may also include an air monitoring system (e.g., the carbon monoxide sensor and moisture sensor 106 of FIGS. 1-3) to automatically track and record any of impurities and contaminants in the breathable air of the air distribution system. The air monitoring system 110 of FIGS. 1-3 may include an automatic shut down feature to suspend air dissemination to the fill stations (e.g., the fill station 102A of FIG. 6A) in a case that any of impurity levels and contaminant levels exceed a safety threshold. The air storage sub-system 1050 may also include a pressure monitoring system (e.g., a pressure sensor 108 of FIG. 1) to continuously track and record the system pressure of the air distribution system (e.g., the air distribution system 150, 250, 350 of FIGS. 1-3). In addition, a pressure switch may be electrically coupled to an alarm system such that the alarm system is set off when the system pressure of the air distribution system (e.g., the air distribution system 150, 250, 350 of FIGS. 1-3) is outside a safety range. The pressure switch (e.g., a pressure sensor 108 of FIG. 1) may electrically transmit a warning signal to an emergency supervising station when the system pressure of the air distribution system (e.g., the air distribution system 150, 250, 350 of FIGS. 1-3) is below the prescribed level.

The air storage sub-system 1050 may include at least one indicator unit to provide status information of the air distribution system (e.g., the air distribution system 150, 250, 350 of FIGS. 1-3) including storage pressure, booster pressure, pressure of the compressed air source, and the system pressure. Further, the air storage sub-system 1050 may also include a selector valve that is accessible by an emergency personnel to isolate the source of compressed air from the air storage sub-system such that the breathable air of the source of compressed air is directly deliverable to the fill site (e.g., the fill site 102B of FIG. 6B, and/or the fill station 102A of FIG. 6A) through the distribution structure. The air storage sub-system 1050 may be housed in a fire rated enclosure that is certified to be rupture containable to withstand elevated temperatures for a period of time.

Figure 11:
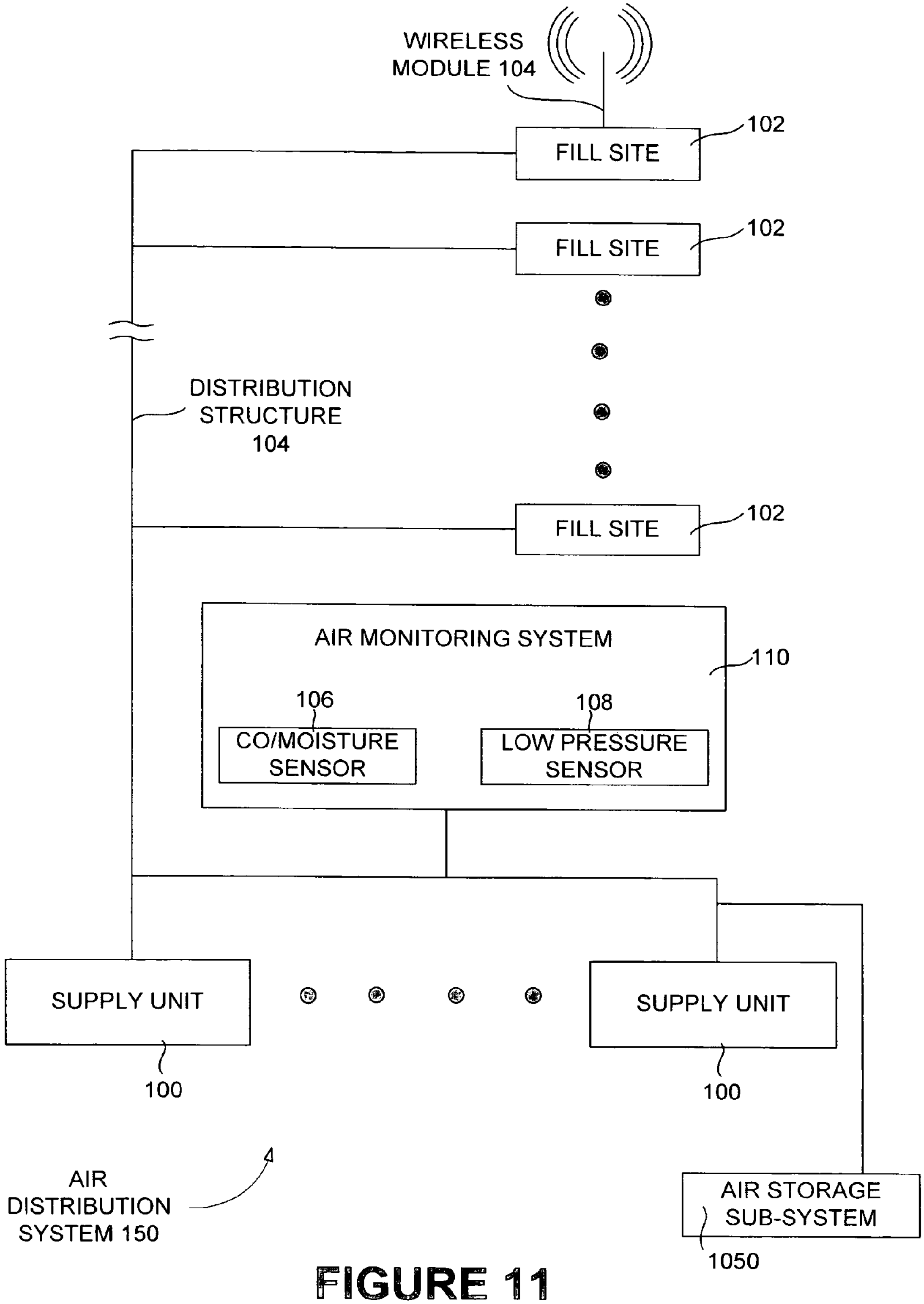
FIG. 11 is a diagram of an air distribution system having an air storage sub-system, according to one embodiment.

FIG. 11 is a diagram of an air distribution system having a air storage sub-system 1050, according to one embodiment.

The air distribution system 150 may include any number of supply units 100, any number of fill sites (e.g., the fill site 102B of FIG. 6B, and/or the fill station 102A of FIG. 6A) that are coupled to the rest of the air distribution system 150 through a distribution structure 104. The air distribution system 150 may also include a air monitoring system 110 having a CO/Moisture sensor 106 and a pressure sensor 108, and/or the air storage sub-system 1050. The air storage sub-system 1050 is as previously described. Air storage tanks 1008 and/or a booster tank 1006 of the air storage sub-system 1050 of FIG. 10 may be supplied with breathable air through a source of compressed air that is coupled to the air distribution system through the supply unit 100 and/or supplied independently of the supply unit 100. The air storage sub-system 1050 may provide a spare source of breathable air to the air distribution system (e.g., the air distribution system 150, 250, 350 of FIGS. 1-3) in addition to an external source of compressed air.

Figure 12:
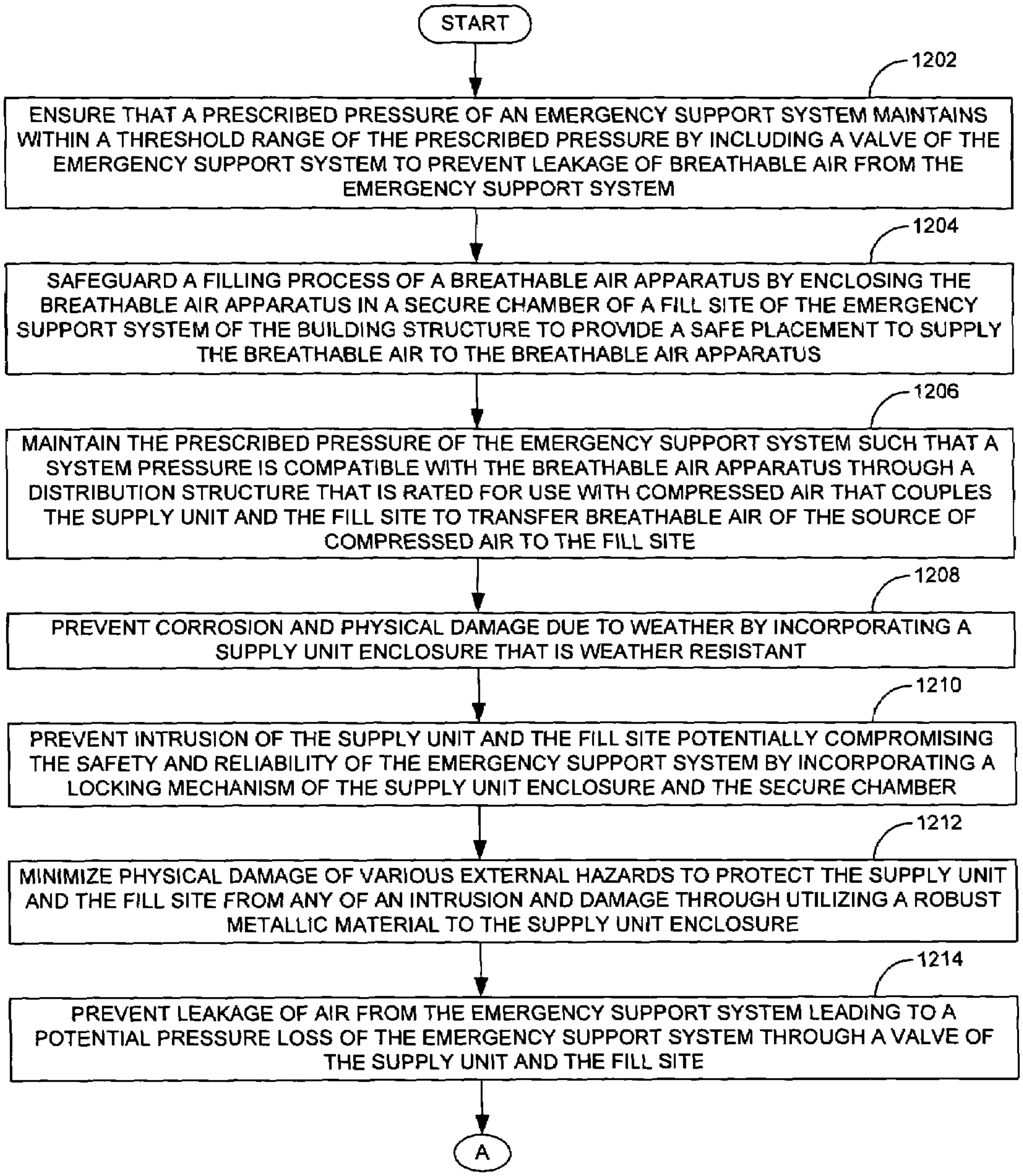
FIG. 12 is a process flow of a safety of a building structure, according to one embodiment.

FIG. 12 is a process flow of a safety of a building structure, according to one embodiment. In operation 1202, a prescribed system pressure of an emergency support system (e.g., the air distribution system 150, 250, 350 of FIGS. 1-3) maintains within a threshold range of the prescribed pressure may be ensured by including a valve (e.g., a valve of a series of valves 410 of FIG. 4) of a supply unit to prevent leakage of breathable air from the emergency support system (e.g., the air distribution system 150, 250, 350 of FIGS. 1-3). In operation 1204, a filling process of a breathable air apparatus may be safeguarded by enclosing the breathable air apparatus in a secure chamber of a fill site of the emergency support system (e.g., the air distribution system 150, 250, 350 of FIGS. 1-3) of the building structure to provide a safe placement to supply the breathable air to the breathable air apparatus.

In operation 1206, the prescribed system pressure of the emergency support system (e.g., the air distribution system 150, 250, 350 of FIGS. 1-3) may be maintained such that the system pressure is compatible with the breathable air apparatus through a distribution structure (e.g., a distribution structure 104 of FIGS. 1-3) that is rated for use with compressed air to connect the supply unit (e.g., the supply unit 100 of FIGS. 1-3) and the fill site to transfer breathable air of the source of compressed air to the fill site. In operation 1208, corrosion and physical damage due to weather may be prevented by incorporating a supply unit enclosure (e.g., the supply unit enclosure 500 of FIG. 5) that is weather resistant. In operation 1210, intrusion of the supply unit (e.g., the supply unit 100 of FIGS. 1-3) and the fill site potentially compromising the safety and reliability of the breathing emergency support system may be prevented by incorporating a locking mechanism (e.g., the locking mechanism 502 of FIG. 5) of the supply unit enclosure (e.g., the supply unit enclosure 500 of FIG. 5) and the secure chamber. In operation 1212, a physical damage of various external hazards to protect the supply unit (e.g., the supply unit 100 of FIGS. 1-3) and the fill site from any of an intrusion and damage may be prevented by utilizing a robust metallic material to the supply unit enclosure (e.g., the supply unit enclosure 500 of FIG. 5).

FIG. 12 is a process flow of a safety of a building structure, according to one embodiment. In operation 1202, a prescribed pressure of an emergency support system maintains within a threshold range of the prescribed pressure may be ensured by including a valve (e.g., a valve of a series of valves 410 of FIG. 4) of the emergency support system (e.g., the air distribution system 150, 250, 350 of FIGS. 1-3) to prevent leakage of breathable air from the emergency support system (e.g., the air distribution system 150, 250, 350 of FIGS. 1-3). In operation 1204, a filling process of a breathable air apparatus may be safeguarded by enclosing the breathable air apparatus in a secure chamber of a fill site of the emergency support system (e.g., the air distribution system 150, 250, 350 of FIGS. 1-3) of the building structure to provide a safe placement to supply the breathable air to the breathable air apparatus.

In operation 1206, the prescribed pressure of the emergency support system (e.g., the air distribution system 150, 250, 350 of FIGS. 1-3) may be maintained such that a system pressure is compatible with the breathable air apparatus through a distribution structure (e.g., a distribution structure 104 of FIGS. 1-3) that is rated for use with compressed air that couples the supply unit (e.g., the supply unit 100 of FIGS. 1-3) and the fill site to transfer breathable air of the source of compressed air to the fill site. In operation 1208, corrosion and physical damage due to weather may be prevented by incorporating a supply unit enclosure (e.g., the supply unit enclosure 500 of FIG. 5) that is weather resistant. In operation 1210, intrusion of the supply unit (e.g., the supply unit 100 of FIGS. 1-3) and the fill site potentially compromising the safety and reliability of the emergency support system (e.g., the air distribution system 150, 250, 350 of FIGS. 1-3) may be prevented by incorporating a locking mechanism (e.g., the locking mechanism 502 of FIG. 5) of the supply unit enclosure (e.g., the supply unit enclosure 500 of FIG. 5) and the secure chamber.

In operation 1212, physical damage of various external hazards may be minimized to protect the supply unit (e.g., the supply unit 100 of FIGS. 1-3) and the fill site from any of an intrusion and damage through utilizing a robust metallic material to the supply unit enclosure (e.g., the supply unit enclosure 500 of FIG. 5). In operation 1214, leakage of air from the emergency support system (e.g., the air distribution system 150, 250, 350 of FIGS. 1-3) leading to a potential pressure loss of the emergency support system (e.g., the air distribution system 150, 250, 350 of FIGS. 1-3) may be prevented through a valve (e.g., a valve of a series of valves 410 of FIG. 4) of the supply unit (e.g., the supply unit 100 of FIGS. 1-3) and the fill site.

Figure 13:
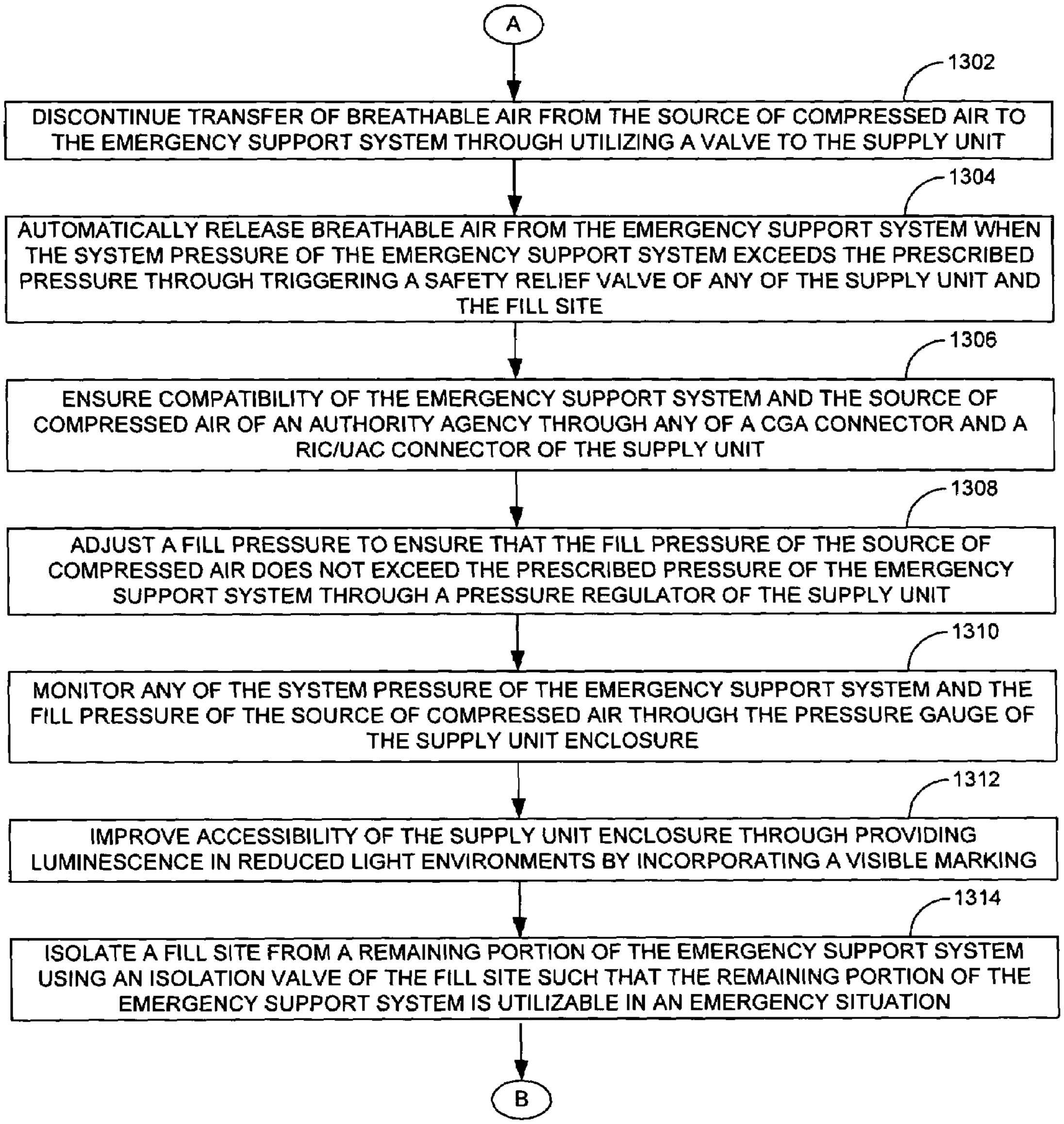
FIG. 13 is a process flow that describes further the operations of FIG. 12, according to one embodiment.

FIG. 13 is a process diagram that describes further the operations of FIG. 12, according to one embodiment. In operation 1302, transfer of breathable air from the source of compressed air to the emergency support system (e.g., the air distribution system 150,250,350 of FIGS. 1-3) may be discontinued through utilizing a valve (e.g., a valve of a series of valves 410 of FIG. 4) to the supply unit (e.g., the supply unit 100 of FIGS. 1-3). In operation 1304, breathable air from the emergency support system (e.g., the air distribution system 150,250,350 of FIGS. 1-3) may be automatically released when the system pressure of the emergency support system (e.g., the air distribution system 150,250, 350 of FIGS. 1-3) exceeds the prescribed pressure through triggering a safety relief valve (e.g., a valve of a series of valves 410 of FIG. 4) of any of the supply unit (e.g., the supply unit 100 of FIGS. 1-3) and the fill site. In operation 1306, compatibility of the emergency support system (e.g., the air distribution system 150,250,350 of FIGS. 1-3) and the source of compressed air of an authority agency may be ensured through any of a CGA connector (e.g., the connector 406 of FIG. 4B) and a RIC (rapid interventions company/crew)/UAC (universal air connection) connector of the supply unit (e.g., the supply unit 100 of FIGS. 1-3).

In operation 1308, a fill pressure may be adjusted to ensure that the fill pressure of the source of compressed air does not exceed the prescribed pressure of the emergency support system (e.g., the air distribution system 150, 250, 350 of FIGS. 1-3) through a pressure regulator of the supply unit (e.g., the supply unit 100 of FIGS. 1-3). In operation 1310, any of the system pressure of the emergency support system (e.g., the air distribution system 150, 250, 350 of FIGS. 1-3) and the fill pressure of the source of compressed air may be monitored through the pressure gauge of the supply unit enclosure (e.g., the supply unit enclosure 500 of FIG. 5). In operation 1312, accessibility of the supply unit enclosure (e.g., the supply unit enclosure 500 of FIG. 5) through providing luminescence in reduced light environments may be improved by incorporating a visible marking. In operation 1314, a fill site from a remaining portion of the emergency support system (e.g., the air distribution system 150, 250, 350 of FIGS. 1-3) may be isolated using an isolation valve (e.g., a valve of a series of valves 410 of FIG. 4) of the fill site such that the remaining portion of the emergency support system (e.g., the air distribution system 150, 250, 350 of FIGS. 1-3) is utilizable in an emergency situation.

Figure 14:
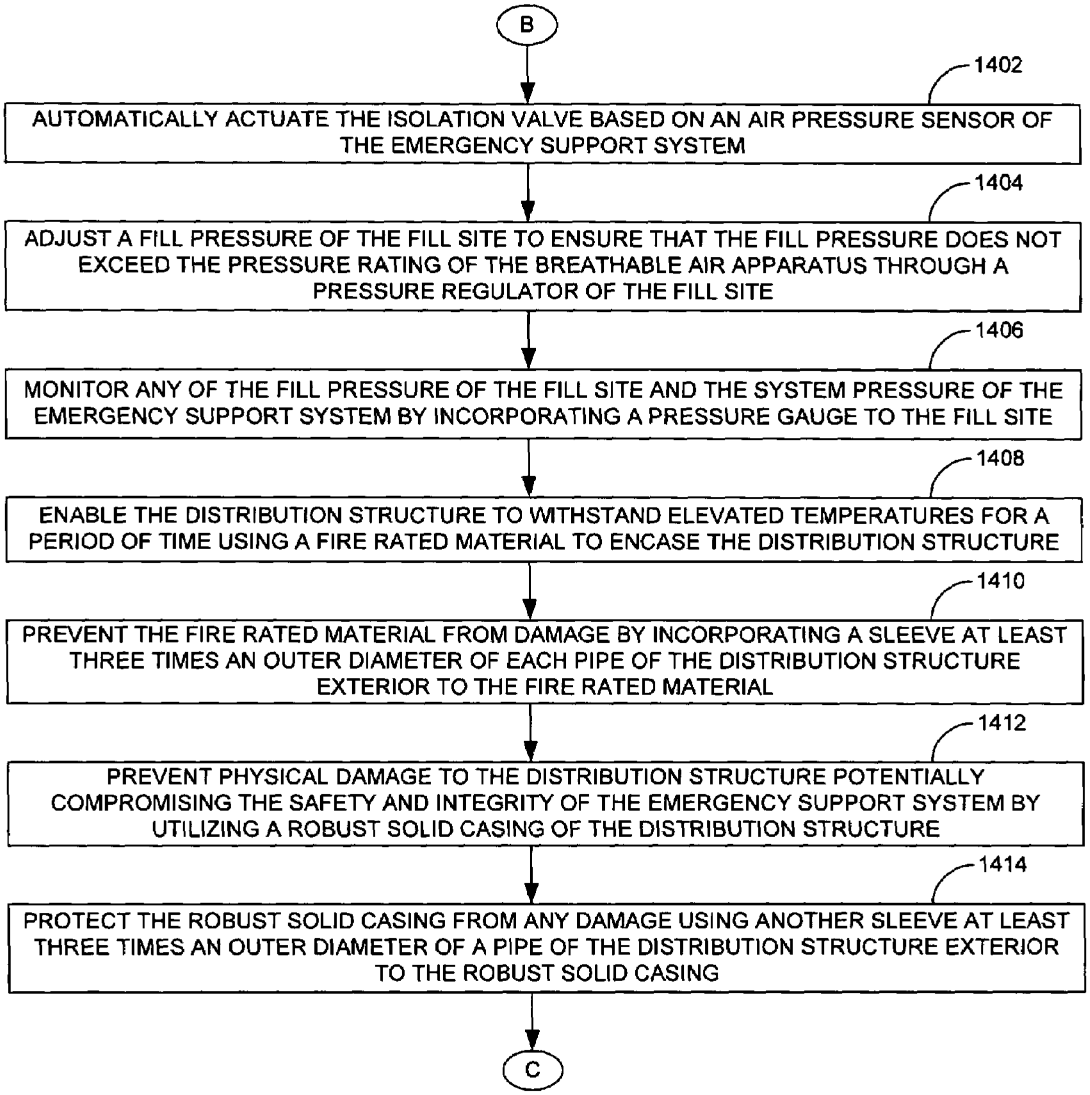
FIG. 14 is a process flow that describes further the operations of FIG. 13, according to one embodiment.

FIG. 14 is a process diagram that describes further the operations of FIG. 13, according to one embodiment. In operation 1402, the isolation valve (e.g., a valve of a series of valves 410 of FIG. 4) based on an air pressure sensor of the emergency support system (e.g., the air distribution system 150, 250, 350 of FIGS. 1-3) may be automatically actuated. In operation 1404, a fill pressure of the fill site to ensure that the fill pressure does not exceed the pressure rating of the breathable air apparatus may be adjusted through a pressure regulator of the fill site. In operation 1406, any of the fill pressure of the fill site and the system pressure of the emergency support system (e.g., the air distribution system 150, 250, 350 of FIGS. 1-3) may be monitored by incorporating a pressure gauge to the fill site.

In operation 1408, the distribution structure (e.g., a distribution structure 104 of FIGS. 1-3) to withstand elevated temperatures for a period of time using a fire rated material may be enabled to encase the distribution structure (e.g., a distribution structure 104 of FIGS. 1-3). In operation 1410, the fire rated material from damage may be prevented by incorporating a sleeve at least three times an outer diameter of each pipe of the distribution structure (e.g., a distribution structure 104 of FIGS. 1-3) exterior to the fire rated material. In operation 1412, physical damage to the distribution structure (e.g., a distribution structure 104 of FIGS. 1-3) potentially compromising the safety and integrity of the emergency support system (e.g., the air distribution system 150, 250, 350 of FIGS. 1-3) may be prevented by utilizing a robust solid casing of the distribution structure (e.g., a distribution structure 104 of FIGS. 1-3). In operation 1414, the robust solid casing may be protected from any damage using another sleeve at least three times an outer diameter of a pipe of the distribution structure (e.g., a distribution structure 104 of FIGS. 1-3) exterior to the robust solid casing.

Figure 15:
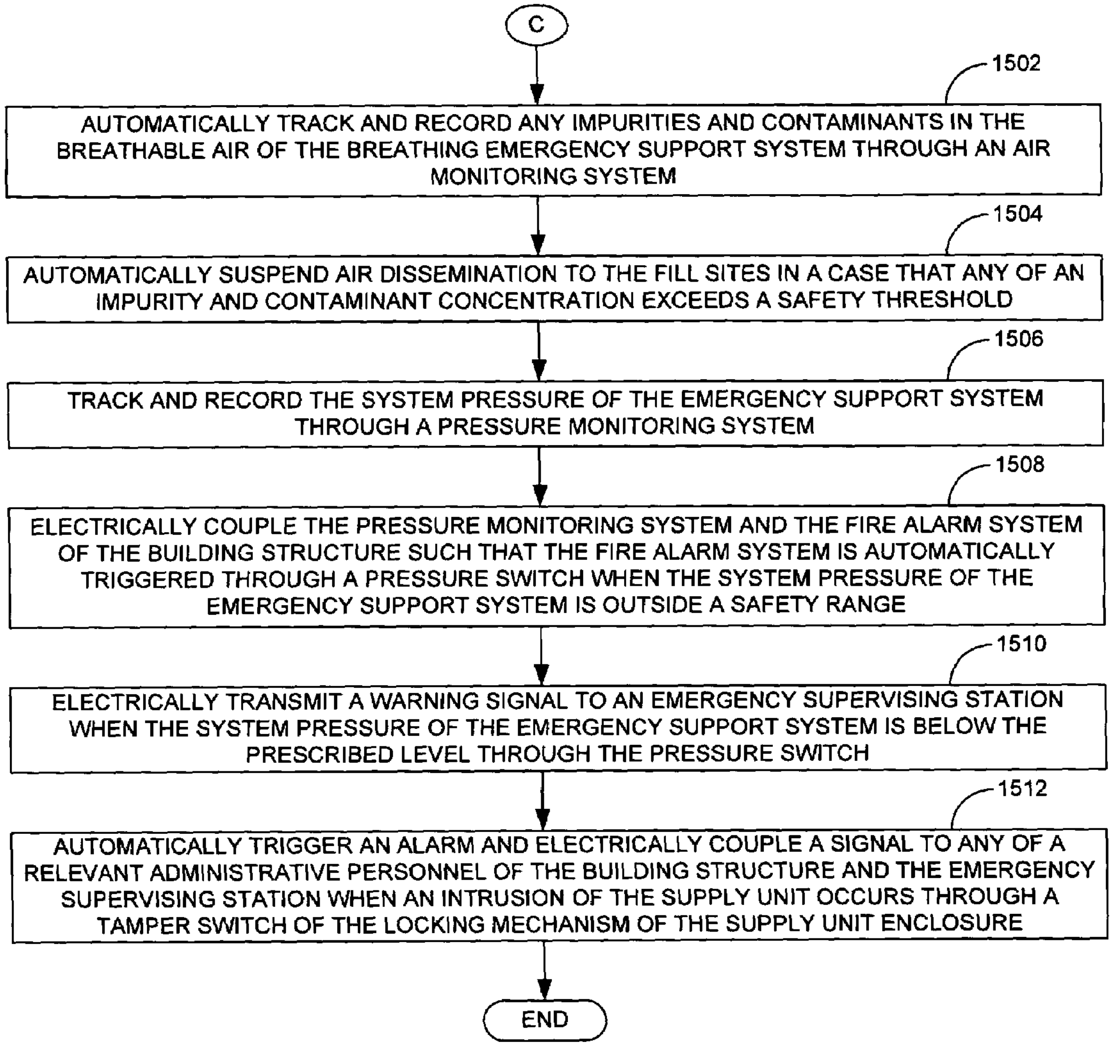
FIG. 15 is a process flow that describes further the operations of FIG. 14, according to one embodiment.

FIG. 15 is a process diagram that describes further the operations of FIG. 14, according to one embodiment. In operation 1502, any impurities and contaminants in the breathable air of the breathing emergency support system (e.g., the air distribution system 150, 250, 350 of FIGS. 1-3) may be automatically tracked and recorded through an air monitoring system. In operation 1504, air dissemination may be automatically suspended to the fill sites in a case that any of an impurity and contaminant concentration exceeds a safety threshold. In operation 1506, the system pressure of the emergency support system (e.g., the air distribution system 150, 250, 350 of FIGS. 1-3) may be tracked and recorded through a pressure monitoring system.

In operation 1508, the pressure monitoring system and the fire alarm system of the building structure may be electrically coupled such that the fire alarm system is automatically triggered through a pressure switch when the system pressure of the emergency support system (e.g., the air distribution system 150, 250, 350 of FIGS. 1-3) is outside a safety range. In operation 1510, a warning signal to an emergency supervising station may be electrically transmitted when the system pressure of the emergency support system (e.g., the air distribution system 150, 250, 350 of FIGS. 1-3) is below the prescribed level through the pressure switch. In operation 1512, an alarm and electrically coupling a signal to any of relevant administrative personnel of the building structure and the emergency supervising station may be automatically triggered when an intrusion of the supply unit (e.g., the supply unit 100 of FIGS. 1-3) occurs through a tamper switch of the locking mechanism (e.g., the locking mechanism 502 of FIG. 5) of the supply unit enclosure (e.g., the supply unit enclosure 500 of FIG. 5).

Although the present embodiments have been described with reference to specific example embodiments, it will be evident that various modifications and changes may be made to these embodiments without departing from the broader spirit and scope of the various embodiments. For example, the various devices, modules, analyzers, generators, etc. described herein may be enabled and operated using hardware circuitry (e.g., CMOS based logic circuitry), firmware, software and/or any combination of hardware, firmware, and/or software (e.g., embodied in a machine readable medium). For example, the various electrical structure and methods may be embodied using transistors, logic gates, and electrical circuits (e.g., application specific integrated ASIC circuitry).

In addition, it will be appreciated that the various operations, processes, and methods disclosed herein may be embodied in a machine-readable medium and/or a machine accessible medium compatible with a data processing system (e.g., a computer system), and may be performed in any order. Accordingly, the specification and drawings are to be regarded in an illustrative rather than a restrictive sense.

What is claimed is:

1. A method of safety of a building structure, comprising:

ensuring that a prescribed pressure of an emergency support system maintains within a threshold range of the prescribed pressure by including a valve of the emergency support system to prevent leakage of breathable air from the emergency support system;

safeguarding a filling process of a breathable air apparatus by enclosing the breathable air apparatus in a secure chamber of a fill site of the emergency support system of the building structure to provide a safe placement to supply the breathable air to the breathable air apparatus; wherein the prescribed pressure of the emergency support system is designated base on a municipality code that specifies a pressure rating of the breathable air apparatus that is used in an authority agency of a particular geographical location; and maintaining the prescribed pressure of the emergency support system such that a system pressure is compatible with the breathable air apparatus through a distribution structure that is rated for use with compressed air that couples the supply unit and the fill site to transfer breathable air of the source of compressed air to the fill site.

2. The method of claim 1 further comprising preventing corrosion and physical damage due to weather by incorporating a supply unit enclosure that is weather resistant.

3. The method of claim 2 further comprising preventing intrusion of the supply unit potentially compromising the safety and reliability of the emergency support system by incorporating a locking mechanism of the supply unit enclosure.

4. The method of claim 3 further comprising minimizing physical damage of various external hazards to protect the supply unit and the fill site from any of an intrusion and damage through utilizing a robust metallic material to the supply unit enclosure.

5. The method of claim 4 further comprising preventing leakage of air from the emergency support system leading to a potential pressure loss of the emergency support system through any of a valve of the supply unit and the fill site.

6. The method of claim 2 further comprising discontinuing transfer of breathable air from the source of compressed air to the emergency support system through utilizing a valve to the supply unit.

7. The method of claim 2 further comprising automatically triggering an alarm and electrically coupling a signal to any of a relevant administrative personnel of the building structure and the emergency supervising station when an intrusion of the supply unit occurs through a tamper switch of the locking mechanism of the supply unit enclosure.

8. The method of claim 1 further comprising automatically releasing breathable air from the emergency support system when the system pressure of the emergency support system exceeds the prescribed pressure through triggering a safety relief valve of any of the supply unit and the fill site.

9. The method of claim 1 further comprising ensuring compatibility of the emergency support system and the source of compressed air of an authority agency through any of a CGA connector and a RIC (rapid interventions company/crew)/UAC (universal air connection) connector of the supply unit.

10. The method of claim 1 further comprising adjusting a fill pressure to ensure that the fill pressure of the source of compressed air does not exceed the prescribed pressure of the emergency support system through a pressure regulator of the supply unit.

11. The method of claim 1 further comprising monitoring any of the system pressure of the emergency support system and the fill pressure of the source of compressed air through the pressure gauge of the supply unit enclosure.

12. The method of claim 1 further comprising improving accessibility of the supply unit enclosure through providing luminescence in reduced light environments by incorporating a visible marking.

13. The method of claim 1 further comprising isolating a fill site from a remaining portion of the emergency support system using an isolation valve of the fill site such that the remaining portion of the emergency support system is utilizable in an emergency situation.

14. The method of claim 13 further comprising automatically actuating the isolation valve based on an air pressure sensor of the emergency support system.

15. The method of claim 1 further comprising adjusting a fill pressure of the fill site to ensure that the fill pressure does not exceed the pressure rating of the breathable air apparatus through a pressure regulator of the fill site.

16. The method of claim 15 further comprising monitoring any of the fill pressure of the fill site and the system pressure of the emergency support system by incorporating a pressure gauge to the fill site.

17. The method of claim 1 further comprising enabling the distribution structure to withstand elevated temperatures for a period of time using a fire rated material to encase the distribution structure.

18. The method of claim 17 further comprising preventing the fire rated material from damage by incorporating a sleeve at least three times an outer diameter of each pipe of the distribution structure exterior to the fire rated material.

19. The method of claim 18 further comprising preventing physical damage to the distribution structure potentially compromising the safety and integrity of the emergency support system by utilizing a robust solid casing of the distribution structure.

20. The method of claim 19 further comprising protecting the robust solid casing from any damage using an another sleeve at least three times an outer diameter of a pipe of the distribution structure exterior to the robust solid casing.

21. The method of claim 1 further comprising automatically tracking and recording any impurities and contaminants in the breathable air of the breathing emergency support system through an air monitoring system.

22. The method of claim 21 further automatically suspending air dissemination to the fill sites in a case that any of an impurity and contaminant concentration exceeds a safety threshold.

23. The method of claim 1 further comprising tracking and recording the system pressure of the emergency support system through a pressure monitoring system.

24. The method of claim 23 further comprising electrically coupling the pressure monitoring system and the alarm system of the building structure such that the alarm system is automatically triggered through a pressure switch when the system pressure of the emergency support system is outside a safety range.

25. The method of claim 24 further comprising electrically transmitting a warning signal to an emergency supervising station when the system pressure of the emergency support system is below the prescribed level through the pressure switch.

* * * * *